United States Patent
Rossi et al.

(10) Patent No.: US 9,632,031 B2
(45) Date of Patent: Apr. 25, 2017

(54) SYSTEM FOR IN VITRO DETECTION AND/OR QUANTIFICATION BY FLUOROMETRY

(71) Applicant: BIOMERIEUX, Marcy-l'Etoile (FR)

(72) Inventors: Véronica Lucia Rossi, Arezzo (IT); Giuseppe Ferorelli, Florence (IT); Massimo Galdiero, San Casciani (IT); Franco Francini, Florence (IT); David Jafrancesco, Florence (IT)

(73) Assignee: BIOMERIEUX, Marcy l'etoile (FR)

( * ) Notice: Subject to any disclaimer, the term of this patent is extended or adjusted under 35 U.S.C. 154(b) by 163 days.

(21) Appl. No.: 14/347,259

(22) PCT Filed: Sep. 25, 2012

(86) PCT No.: PCT/FR2012/052136
§ 371 (c)(1),
(2) Date: Mar. 26, 2014

(87) PCT Pub. No.: WO2013/045807
PCT Pub. Date: Apr. 4, 2013

(65) Prior Publication Data
US 2014/0252246 A1 Sep. 11, 2014

(30) Foreign Application Priority Data
Sep. 26, 2011 (FR) ...................... 11 58532

(51) Int. Cl.
*G01N 21/64* (2006.01)
(52) U.S. Cl.
CPC ....... *G01N 21/6486* (2013.01); *G01N 21/645* (2013.01); *G01N 21/6408* (2013.01)
(58) Field of Classification Search
CPC ........... G01N 21/6486; G01N 21/6408; G01N 21/645
(Continued)

(56) References Cited

U.S. PATENT DOCUMENTS

| 5,257,202 A | 10/1993 | Feddersen et al. |
| 5,757,013 A | 5/1998 | Groger et al. |

(Continued)

FOREIGN PATENT DOCUMENTS

| EP | 0 241 268 A2 | 10/1987 |
| EP | 0 864 089 B1 | 7/2002 |

(Continued)

OTHER PUBLICATIONS

International Search Report issued in International Patent Application No. PCT/FR2012/052136 dated Nov. 11, 2012 (with translation).

*Primary Examiner* — David Porta
*Assistant Examiner* — Gisselle Gutierrez
(74) *Attorney, Agent, or Firm* — Oliff PLC

(57) ABSTRACT

The invention relates to a system for the in vitro detection and/or quantification, by fluorometry, of at least one analyte in a sample of fluid constituting a biological material, in particular for an immunological test, including a radiation source, followed by an optical splitter for splitting the main beam into a sample-energizing beam and a reference beam, with a first photodetector means for detecting a fluorescence ray emitted by the sample and a second photodetector means for the reference beam, said system also including a generator outputting a sinusoidal carrier signal and at least one digital demodulation signal, and a digital processing means for processing, by demodulation, the signals from the two photodetector means in order to extract a fluorescence value that is characteristic of the amplitude of the fluorescence ray and a second reference value that is characteristic of the amplitude of the reference beam.

12 Claims, 8 Drawing Sheets

(58) Field of Classification Search
USPC ............................. 250/458.1, 459.1, 208.2
See application file for complete search history.

(56) References Cited

U.S. PATENT DOCUMENTS

| | | | | |
|---|---|---|---|---|
| 5,818,582 | A * | 10/1998 | Fernandez | ............ G01J 3/4406 |
| | | | | 250/458.1 |
| 6,157,037 | A * | 12/2000 | Danielson | .......... G01N 21/6408 |
| | | | | 250/458.1 |
| 2007/0259451 | A1* | 11/2007 | Heanue | .............. G01N 21/6408 |
| | | | | 436/518 |
| 2010/0324834 | A1 | 12/2010 | Treptow et al. | |
| 2011/0001963 | A1 | 1/2011 | Durack | |
| 2011/0066014 | A1* | 3/2011 | Bechtel | ................ A61B 5/0059 |
| | | | | 600/323 |

FOREIGN PATENT DOCUMENTS

| | | |
|---|---|---|
| EP | 0 871 863 B1 | 7/2002 |
| WO | WO 00/37850 A1 | 6/2000 |
| WO | WO 2004/055502 A2 | 7/2004 |

\* cited by examiner

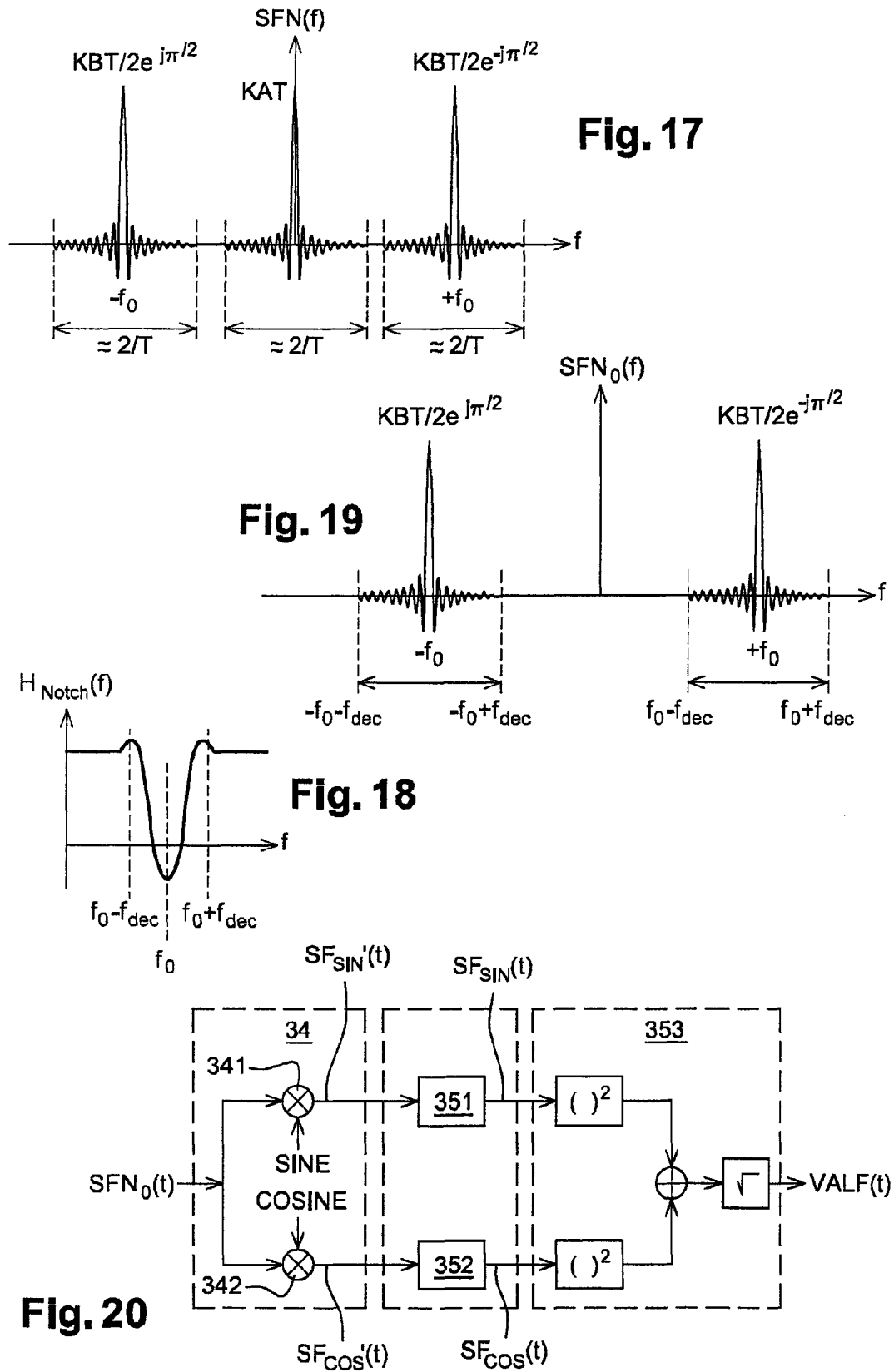

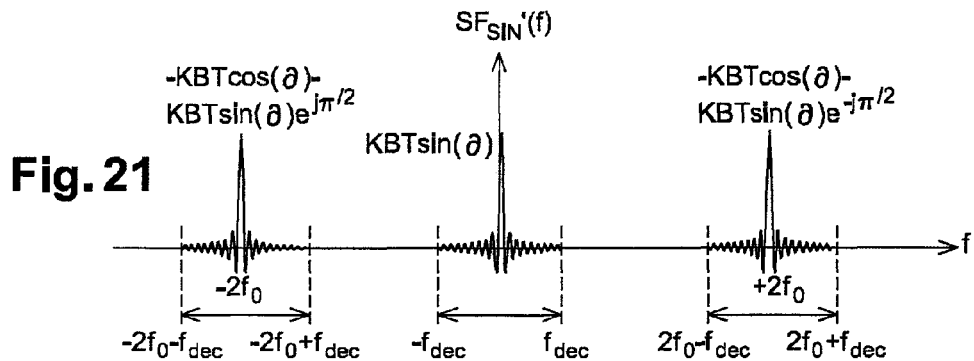
Fig. 21
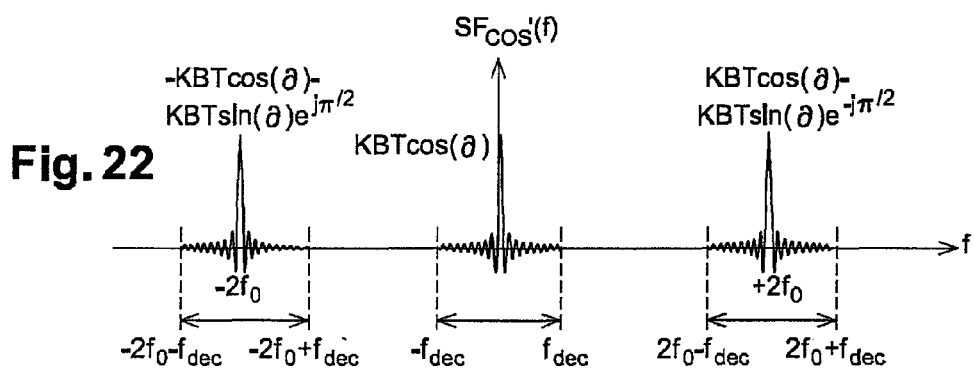
Fig. 22
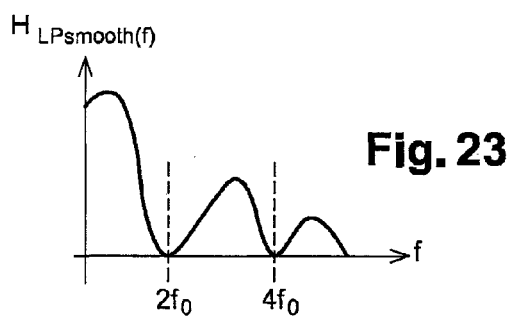
Fig. 23
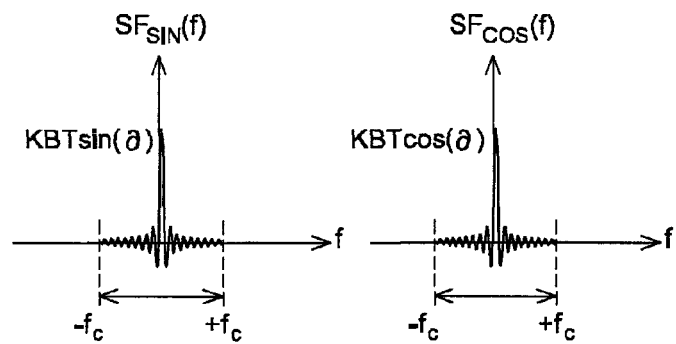
Fig. 24  Fig. 25

SYSTEM FOR IN VITRO DETECTION AND/OR QUANTIFICATION BY FLUOROMETRY

The present invention relates to a system for the in vitro detection and/or quantification by fluorometry of at least one analyte in a sample (E) of fluid constituting a biological material.

The present invention can be used in automated instruments for in vitro diagnosis in the clinical or the industrial field.

In the clinical field, the diagnosis is carried out from a human biological sample (urine, blood, saliva, pus, cerebrospinal fluid, etc.), for detecting or quantifying analytes from an external micro-organism or not (bacteria, virus, parasite, antibody, etc.) in the form of immunological tests or molecular biology tests.

In the industrial field, the diagnosis is carried out from a sample of food, pharmaceutical or cosmetic product to control the microbiological quality of the product in the form of microbiological tests. Such microbiological tests generally check either the sterility (no microorganism should be present), or the absence of pathogenic bacteria (source of an infection), or even that a commensal bacteria (normally present in humans and banal in low concentration) is only present below a certain threshold.

The invention can also be used in the field of dynamic analyses, that is to say in real time, in this instance in immunological tests and molecular biology tests where the immunological/biological reactions may be managed or controlled over time.

The invention more particularly relates to a system for the in vitro detection and/or quantification by fluorometry comprising:
- light radiation source emitting a main beam in a given wavelength called emission;
- an optical splitter arranged at the output of the radiation source for splitting the main beam into a first sample-energizing beam and a second reference beam;
- a first photodetector means designed for providing a first analog detection signal in response to detecting a fluorescence ray emitted by the sample, in a so-called fluorescence wavelength as a result of the excitation induced by the first energizing beam;
- a second photodetector means designed for providing at the output a second analog detection signal in response to a detection of the second reference beam.

Such in vitro detection and/or quantification systems, are particularly known in automated in vitro diagnosis instruments by fluorometry, such as for example in documents EP 0864 089 B1, EP 0871 863 B1, EP 0 241 268 A1, and WO 2004055502 A2, which use radiation sources of pulsed light source type, laser lamps or arc lamps.

Typically, the analysis of signals from the two photodetector means is carried out by an analog processing, with, in particular an algorithm for detecting the fluorescence peak representing the presence/quantity of analytes to detect. The drawback of such an analog processing substantially resides in its limitations for reducing noise and hence in increasing the signal-to-noise ratio.

The prior art may also be illustrated by the teaching of patent application U.S. Pat. No. 5,757,013 A which discloses an apparatus for measuring fluorescence decay, which implements a digital processing based on a fluorescence signal and a reference signal, where the reference signal substantially serves to measure a phase shift for the fluorescence signal, with the implementation of the calculation of an internal product between the fluorescence and reference signals demodulated at a frequency different from the carrier frequency of the drive signal of the light source; this calculation allowing to determine such a phase shift and to deduce the fluorescence decay thereof. The purpose of the measuring apparatus of application U.S. Pat. No. 5,757,013 A is to determine the fluorescence decay, without reference to the concentration of fluorophore in the sample.

The prior art also includes the teaching of document WO 0037850 A1 which relates to an apparatus intended to measure the emission delay time during the irradiation of a sample, comprising a system generating first and second digital input signals, a device for converting these two signals into analog sinusoidal signals, a radiation source modulated at a specific frequency and which irradiates the sample, thus generating an emission by the sample. The apparatus also comprises a detector of the emission from the sample and which generates a first output signal having a phase shift with respect to the phase of the first input signal, and a device which allows to digitize the first and second analog output signals, a mixer receiving the output signals and comparing the signal phase in order to generate a signal indicating the phase change. A feedback device distorts, on the basis of the mixer signal, the phase of the second input signal in order to place the first and second output signals in quadrature.

The purpose of the present invention is to provide an in vitro detection and/or quantification system by fluorometry comprising signal processing means ensuring a detection/quantification of the analyte with an improved sensitivity obtained by an increase in the signal-to-noise ratio.

In fact, it proposes an in vitro detection and/or quantification system by fluorometry of at least one analyte in a sample of fluid, including:
- a radiation source emitting a main beam in a given wavelength called emission;
- an optical splitter arranged at the output of the radiation source for splitting the main beam into a first sample-energizing beam and a second reference beam;
- a first photodetector means designed for providing a first analog detection signal in response to detecting a fluorescence ray emitted by the sample, in a so-called fluorescence wavelength as a result of the excitation induced by the first energizing beam;
- a second photodetector means designed for providing at the output a second analog detection signal in response to a detection of the second reference beam.

This system being remarkable in that it includes:
- a generator outputting a sinusoidal carrier signal at a so-called predefined carrier frequency, and at least one digital demodulation signal at this same carrier frequency;
- a digital/analog conversion means connected to the generator for converting the sinusoidal carrier signal to an analog modulation signal at the carrier frequency;
- an amplitude modulator connected to the digital/analog conversion means and to the radiation source to modulate in amplitude the main beam at the carrier frequency by applying the analog modulation signal on said radiation source;
- digital/analog conversion means connected to the photodetector means to convert the first analog detection signal into a first digital so-called fluorescence signal and the second analog detection signal into a second digital reference signal;
- digital processing means connected to the generator and to the analog/digital conversion means, designed, on the one hand to process the first digital fluorescence signal by demodulation at the carrier frequency in order to calculate a first so-called fluorescence value characteristic of the amplitude of the fluorescence ray and, on the other hand, process the second digital reference signal by demodulation at the carrier frequency in order to calculate a second so-called reference value characteristic of the amplitude of the reference beam;

a means for comparing the first fluorescence value and the second reference value to calculate a final result for establishing the detection and/or quantification of the analyte.

Thus, the system according to the invention performs a digital processing by amplitude modulation and demodulation, allowing to reach particularly interesting signal-to-noise ratios.

Such a digital processing is preferably carried out with a light-emitting diode (LED), in particular, in the UV spectrum, as radiation source, as light-emitting diodes are particularly suitable for use with a modulated drive. With a light-emitting diode, it may be particularly ensured a set of light flashes of amplitude of well defined and controlled temporal and frequential forms, the flashes capable of being spaced temporally apart from each other in a controlled and precise manner. With such a drive possibility of the light-emitting diode, the following digital processing allows to reject/limit noise.

It is understood that the first digital fluorescence signal and the second digital reference signal are demodulated separately at the same frequency corresponding to the carrier frequency of the sinusoidal carrier signal prior to carrying out the comparison which will allow to extract the final result which preferably comes in the form of a relative fluorescence unit (RFU).

In a particular embodiment, the digital processing means comprise:
  a first demodulation means designed for demodulating the first digital fluorescence signal by multiplying it by at least one digital demodulation signal at the carrier frequency, in order to generate at least one first demodulated fluorescence signal; and
  a first calculation means designed to calculate, based on at least one first demodulated fluorescence signal, the first fluorescence value.

According to a feature, the first demodulation means comprises:
  a first multiplier by a digital demodulation signal at the carrier frequency and in phase with the sinusoidal carrier signal, said first multiplier being possibly followed by a first low-pass filter at a cut-off frequency lower than the carrier frequency, in order to output a first so-called in-phase demodulated fluorescence signal; and
  a second multiplier by a digital demodulation signal at the carrier frequency and in phase quadrature with respect to the sinusoidal carrier signal, said second multiplier possibly being followed by a second low-pass filter at the same cut-off frequency, in order to output a first so-called phase quadrature demodulated fluorescence signal;
  and furthermore, the first calculation means, at the output of said first and second multipliers, calculates the first fluorescence value corresponding to the module of sum of the first in phase demodulated fluorescence signal and the first phase quadrature demodulated fluorescence signal.

With this feature, the demodulation process corresponds to a coherent demodulation in phase and in phase quadrature which is particularly advantageous for improving the signal-to-noise ratio.

The system possibly includes at least one low-pass filter, at a cut-off frequency lower than the carrier frequency, at the output of the first demodulation means in order to filter the or each first demodulated fluorescence signal.

According to another feature, the digital processing means comprise, in input of the first and second multipliers:
  a notch filter centered on the carrier frequency in order to filter the first digital fluorescence signal and output a first filtered intermediate signal; and
  a subtracter performing the subtraction of the first digital fluorescence signal and the first filtered intermediate signal, in order to generate a first filtered fluorescence signal, this first filtered fluorescence signal being injected in said first and second multipliers of the first demodulation means.

The notch filter associated with the subtracter forms in the end a band-pass filter excluding the frequential incoming component at the carrier frequency.

In a particular embodiment, the digital processing means include:
  a second demodulation means designed to demodulate the second digital reference signal, by multiplying it by at least one digital demodulation signal at the carrier frequency, in order to generate at least one second demodulated reference signal; and
  a second calculation means designed to calculate, based on at least one second demodulated reference signal, the second reference value.

In this embodiment, the second processing means applies a demodulation processing on the second digital reference signal, with the advantages pertaining to this type of process for improving the signal-to-noise ratio.

According to a possibility of the invention, the second demodulation means includes:
  a first multiplier by a digital demodulation signal at the carrier frequency and in phase with the sinusoidal carrier signal, said first multiplier being possibly followed by a first low-pass filter at a cutoff frequency lower than the carrier frequency, so as to output a second so-called in phase demodulated reference signal; and
  a second multiplier by a digital demodulation signal at the carrier frequency and in phase quadrature with respect to the sinusoidal carrier signal, said second multiplier being possibly followed by a second low-pass filter at the same cutoff frequency so as to output a second so-called phase quadrature demodulated reference signal;
  and the second calculation means, at the output of said first and second multipliers, calculates the second reference value corresponding to the module of the sum of the second in phase demodulated reference signal and the second in phase quadrature demodulated reference signal.

According to another possibility of the invention, the digital processing means comprise, in input of these first and second multipliers:
  a notch filter centered on the carrier frequency so as to filter the second digital reference signal and output a second filtered intermediate signal; and
  a subtracter performing the subtraction of the second digital reference signal and the second filtered intermediate signal so as to generate a second filtered reference signal, this second filtered reference signal being injected in said first and second multipliers of the second demodulation means.

Advantageously, the system further comprises, interposed between the radiation source and the optical splitter, an optical band-pass filter substantially centered on the emission wavelength.

The use of such an optical band-pass filter allows to increase the signal at the photodetector means, by improving at the source the signal by filtering the interfering frequencies.

According to a feature, the system further comprises, interposed between the sample and the first photodetector means, an optical band-pass filter substantially centered on the fluorescence wavelength.

The use of such an optical band-pass filter allows to increase the signal at the first photodetector means, by filtering the interfering frequencies.

According to a feature, the system further comprises, interposed between the optical band-pass filter and the first photodetector means, a waveguide achieved in the form of a guiding cone.

In a particular embodiment, the system further comprises, interposed between the optical splitter and the second photodetector means, an optical low-pass filter which exhibits a low-wavelength cutoff substantially lower than the emission wavelength.

According to a possibility of the invention, the system further comprises, interposed between the optical low-pass filter and the second photodetector means, a waveguide achieved in the form of a guiding cone.

According to another possibility of the invention, the sinusoidal carrier signal is in the form of a set of several periodic sinusoidal iterations at the carrier frequency, the time difference between two consecutive iterations being higher than the period of sinusoidal iterations.

Other characteristics and advantages of the present invention will become apparent upon reading the following detailed description, of a non limiting implementation, made with reference to the accompanying drawings in which:

FIG. 17 is a graph illustrating the variation curve of the first digital fluorescence signal SFN(f) according to the frequency f;

FIG. 18 is a graph illustrating the variation curve of the function $H_{NOTCH}$ (f) according to the frequency f;

FIG. 19 is a graph illustrating the variation curve of the first filtered fluorescence signal $SFN_0$(f) according to the frequency f;

FIG. 20 is a schematic view of a set of two multipliers, two low-pass filters and a calculation means for a first module for acquiring/processing the digital fluorescence signal;

FIG. 21 is a graph illustrating the variation curve of the intermediate demodulated signal in phase $SF_{SIN''}$(f) according to the frequency f;

FIG. 22 is a graph illustrating the variation curve of the intermediate demodulated signal in phase quadrature $SF_{COS'}$(f) according to the frequency f;

FIG. 23 is a graph illustrating the variation curve of the function $H_{LPsmooth}$(f) according to the frequency f;

FIG. 24 is a graph illustrating the variation curve of the first demodulated signal in phase $SF_{SIN}$(f) according to the frequency f;

FIG. 25 is a graph illustrating the variation curve of the first demodulated signal in phase quadrature $SF_{COS}$(f) according to the frequency f;

Figure 1:
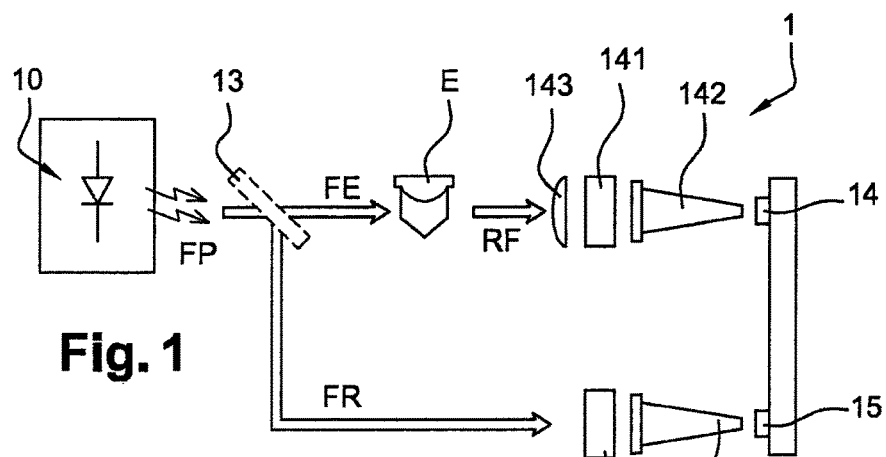
FIG. 1 is a schematic view of a system in accordance with the invention.
Figure 2:
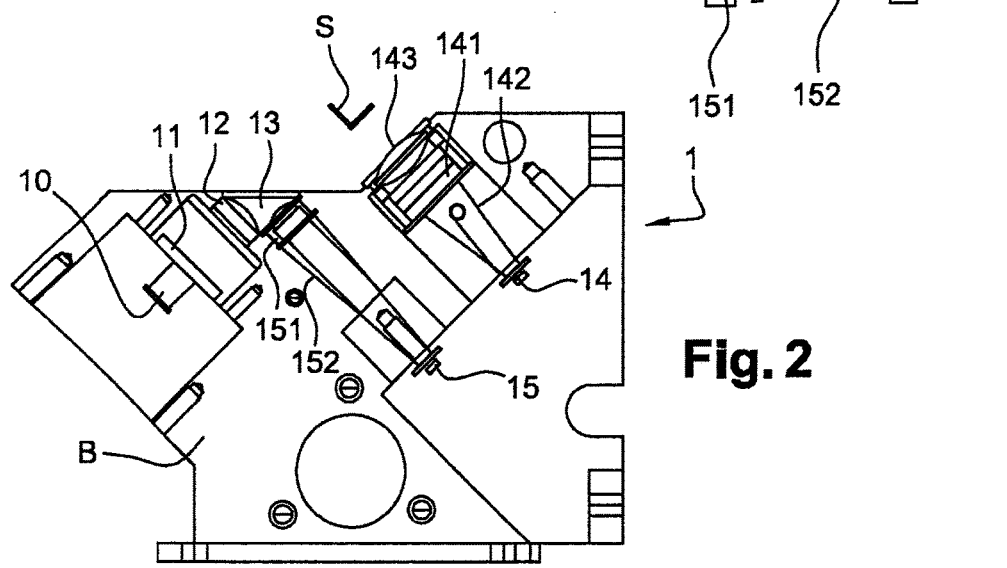
FIG. 2 is a schematic view of a system in accordance with the invention according to a first configuration.
Figure 3:
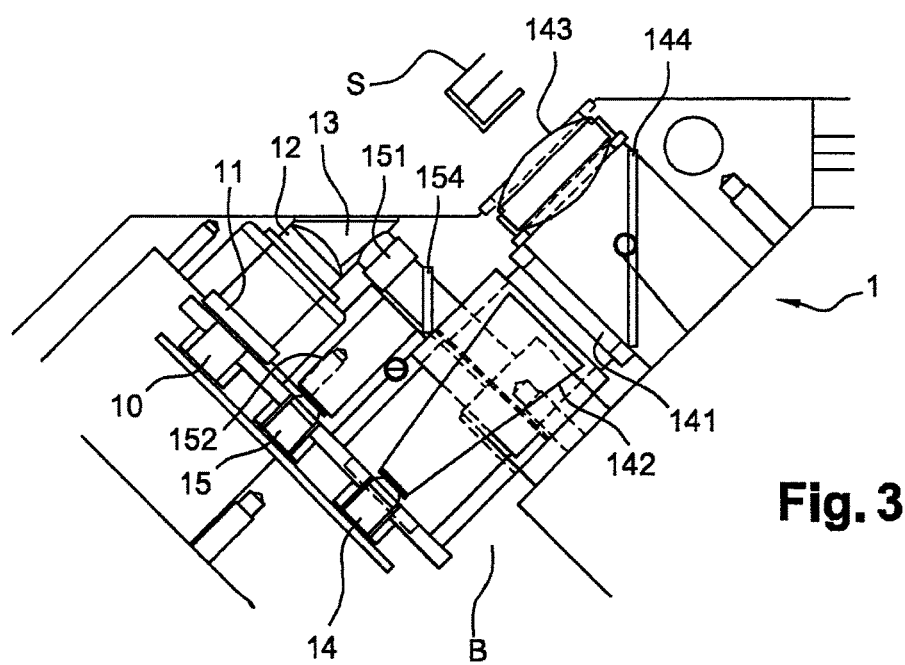
FIG. 3 is a schematic view of a system in accordance with the invention according to a second configuration.

The first part of the following description relates to the architectural or structural part of the system 1 in accordance with the invention for the in vitro detection and/or quantification by fluorometry of at least one analyte in a sample E of fluid constituting a biological material. The FIGS. 1 to 3 schematically illustrate the architecture of such a system 1 in accordance with the invention and designed for fitting an automated in vitro diagnosis instrument.

This system 1 is intended in particular for analyzing by fluorometry the fluorescent radiation emitted during an immunological test based on 4-methylumbelliferone (4-MU), as resulting from the hydrolysis of the substrate 4-methylumbelliferyl-phosphate (4-MUP) in the sample E of fluid. Thus, the function of this system is to perform an instantaneous measurement of the fluorescent radiation emitted by the 4-MU in the sample E, under the incidence of the energizing beam suitable for exciting the 4-MU, while avoiding to excite the substrate 4-MUP.

This system 1 comprises a rack B supporting a light radiation source 10 emitting a main beam FP. The radiation source 10 is constituted of an electroluminescent diode emitting in the ultraviolet (UV LED).

Figure 4:
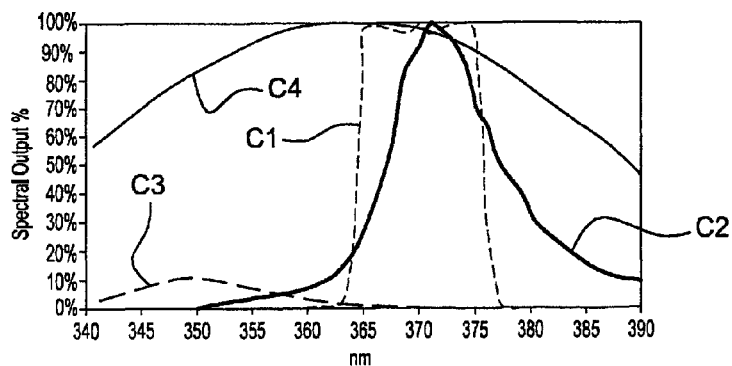
FIG. 4 is a graph respectively illustrating the transmission spectrum of an optical band-pass filter and the emission spectrum of a UV diode fitting both a system in accordance with the invention, and the energizing spectrums 4-MU and 4-MUP.

The curves C3 and C4 of FIG. 4 illustrate respectively the energizing spectrums of 4-MUP and 4-MU, according to the wavelength (in nm), which exhibit excitation peaks respectively at 350 nm and 365-370 nm. In order to obtain an emission of a fluorescence ray of 4-MU, it is thus necessary to have a diode which emits a main beam FP in the wavelength range of 365-370 nm.

Although the maximum of the excitation peak of 4-MU is located at 365 nm, it is nevertheless preferable that the main beam FP be centered around 370 nm. In fact, a wavelength of 365 nm for the main beam would excite the 4-MUP too much and thus cause an interference detrimental to the proper analysis of the fluorescence signal of the 4-MU. The electroluminescent diode 10 thus preferably emits in a wavelength of around 370 nm; a diode being theoretically monochromatic.

For example, the diode 10 is constituted of a reference diode "NSHU591A Rank 6" commercialized by the NICHIA Corporation, emitter in the wavelength range 370-375 nm, with a spectral half-width of 15 nm. The curve C2 of FIG. 4 illustrates the spectrum of the reference diode NSHU591A according to the wavelength (in nm).

In order to answer the issue of limiting the main beam FP wavelength around 370 nm, the system 1 further comprises an optical band-pass filter 11 centered on the wavelength of 370 nm; this optical band-pass filter 11 being arranged in front of the diode 10.

For example, the optical band-pass filter 11 may be constituted of an optical band-pass filter of reference "Biom-0007 Rev A—370/10" commercialized by the Semrock company, having the following features:
  central wave length (CWL): 370 nm;
  full width at half the transmission peak (FWHM for Full Width at Half Maximum): 11.5 nm±1 nm;
  peak transmission percentage: 90%;
  optical density (OD) >5 for the 300-355 nm range; and
  optical density (OD) >4 for the 385-1000 nm range.

The curve C1 of FIG. 4 illustrates the transmission spectrum of such an optical band-pass filter 11 according to the wavelength (in nm).

Of course, other pairs of diodes 10 and optical band-pass filters 11 may be considered. In all cases, it is essential to select a diode by its spectral emission band according to the spectral transmission band of the optical band-pass filter or conversely, given that these two relatively narrow spectral bands must coincide.

In order to channel the radiation emitted by the diode 10 and filtered by the optical band-pass filter 11, the system 1 comprises, behind the optical band-pass filter 11, an objective lens 12, such as a convex plane lens particularly suitable for a UV diode.

The system 1 further comprises, behind the objective lens 12, an optical splitter 13 for splitting the main beam FP into a first sample-energizing beam FE and a second reference beam FR. This optical splitter 13 is for example achieved in the form of a semi-reflecting mirror or semi-reflecting prism or beam splitter.

Figure 5:
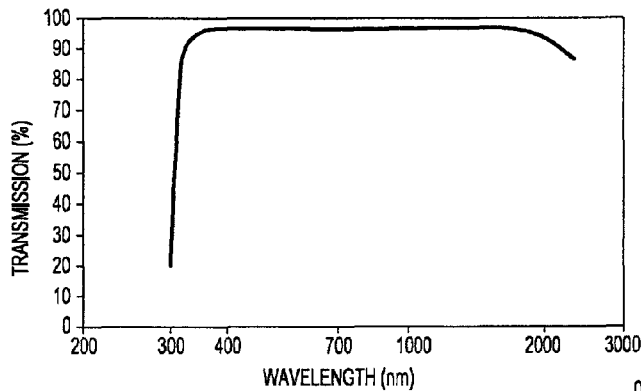
FIG. 5 is a schematic graph of a transmission spectrum of an optical splitter fitting a system in accordance with the invention.

For example, the optical splitter 13 may be constituted of a semi-reflecting glass prism of BK7 type having a refractive (or transmission) rate of around 95%, and a reflecting rate of around 5%; the first energizing beam FE corresponding to the refracted (or transmitted) beam by the optical splitter 13 and the second reference beam FR corresponding to the beam reflected by the optical splitter 13. FIG. 5 illustrates the transmission spectrum of such a semi-reflecting glass prism of BK7 type.

As described previously, it is essential to recover a portion of the main beam FP in the form of a second reference beam FR, to achieve the detection of the intensity of the diode 10 and control its stability. Furthermore, the refraction (or transmission) rate will be later taken into account in the determination of the energy transmitted to the sample E.

The system 1 also comprises a support S for the sample E, this support S being positioned so that the first energizing beam FE irradiates the sample E and excites the 4-MU which will then emit a fluorescence ray RF as a result of the excitation induced by this first energizing beam FE.

Figure 7:
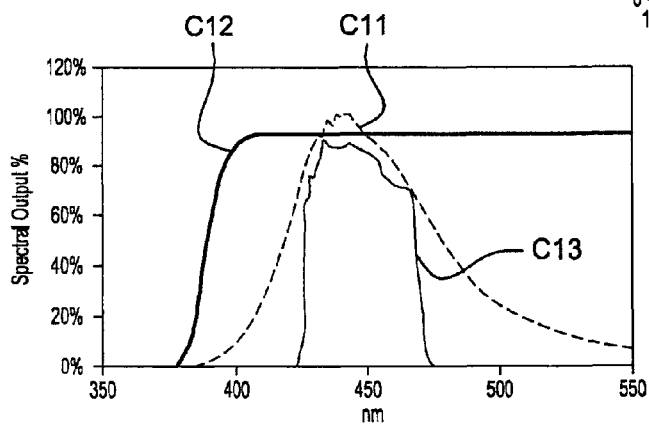
FIG. 7 is a schematic graph of the fluorescence spectrum of 4-MU, and the transmission spectrum of another optical band-pass filter and a guiding cone both fitting a system in accordance with the invention.

The fluorescence ray RF of the 4-MU (or fluorescence signal of the 4-MU) has an emission peak at around 450 nm. The curve C11 of FIG. 7 illustrates the fluorescence spectrum of the 4-MU which exhibits an emission peak at around 450 nm.

The system 1 comprises a first photodetector means 14 designed for detecting this fluorescence ray FR, and outputting a first analog detection signal SAD1 in response to a detection of this fluorescence ray RF. The first photodetector means 14 is for example of photodiode type, and the first analog detection signal SAD1 corresponds to a diode current (intensity in amperes).

Figure 6:
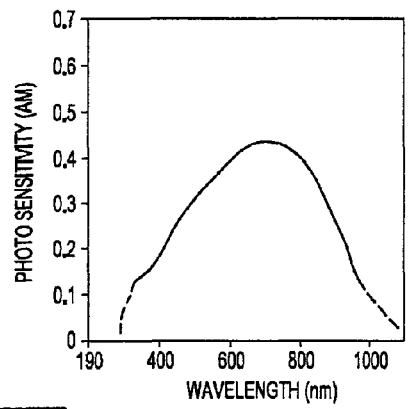
FIG. 6 is a schematic graph of the variation of the photosensitivity of a photodiode fitting a system in accordance with the invention, based on the wavelength of the detected radiation at a temperature of 25° C.

For example, the first photodetector means 14 is constituted of a silicon photodiode of reference "S1227 BR", commercialized by the Hamamatsu company, and whereof the FIG. 6 illustrates the variation of the photosensitivity according to the wavelength of the detected radiation, at a temperature of 25° C. Thus, it is to be noted that such a silicon photodiode exhibits a photosensitivity in the magnitude of 0.25 A/W for a wavelength in the magnitude of 450 nm, corresponding as a reminder to the wavelength of the emission peak of the fluorescence ray RF of the 4-MU.

So that the first photodetector means 14 be sensitive to the fluorescence ray RF of the 4-MU, the system 1 comprises, in a channel for guiding the fluorescence ray RF placed between the sample E and the first photodetector means 14, an optical band-pass filter 141 and a waveguide 142.

The optical band-pass filter 141 is substantially centered on the wavelength of the fluorescence ray RF, and hence on the wavelength of 450 nm for the detection of the fluorescence of the 4-MU.

For example, the optical band-pass filter 141 exhibits the following optical features:
  central wavelength: 450 nm±5 nm;
  width of the bandwidth: 40 nm±4 nm;
  percentage of transmission at the central wavelength >45% in the magnitude of 80 to 90%.

The curve C13 of FIG. 7 illustrates the transmission spectrum of such an optical band-pass filter 141, which exhibits a transmission peak coinciding substantially with the fluorescence spectrum peak of the 4-MU illustrated on the curve C11.

The waveguide 142 is preferably achieved in the form of a guiding cone or optical cone, for example of polymethyl methacrylate (PMMA), in order to channel the fluorescence ray RF filtered by the optical band-pass filter 141 in the direction of the first photodetector means 14.

For example, the guiding cone 142 may exhibit a feature of the high-pass filter, with a low-frequency cutoff lower than the wavelength of the fluorescence ray RF, in this instance lower than 450 nm. The curve C12 of FIG. 7 illustrates the transmission spectrum of such a guiding cone 142 which exhibits a low-wavelength cutoff in the magnitude of 375-385 nm.

FIG. 7 illustrates the fact that the guiding cone 142 does not affect the fluorescence ray RF in spectrum terms, and that the selected optical band-pass filter 141 is suitable for detection by the first photodetector means 14. In fact, the optical features of the optical band-pass filter 141 substantially coincide with the emission spectrum of the fluorescence ray RF and highly reduce the interfering energizing signals capable of being emitted by the irradiated sample E.

The system also comprises an objective lens 143 arranged in input of the channel for guiding the fluorescence ray RF, before the optical band-pass filter 141 to make the fluorescence ray RF converge towards the guiding cone 142; this objective lens 143 may be of biconvex lens type.

Thus, the first energizing beam FE interacts with the medium contained in the sample E, thus causing the emission of a fluorescence ray RF which is collected by the lens 143, before passing through the optical band-pass filter 141 and the guiding cone 142 to the first photodetector means 14.

The system 1 also comprises a second photodetector means 15 designed to detect the second reference beam FR, and output a second analog detection signal SAD2 in response to a detection of this second reference beam FR. The second photodetector means 15 is for example of the photodiode type, and the second analog detection signal SAD2 corresponds to a diode current (intensity in amperes).

For example, the second photodetector means 15 is of the same type as the first photodetector means 14 and can be constituted of a silicon photodiode of reference "S1227 BR" commercialized by the Hamamatsu company, and whereof FIG. 6 illustrates the variation of the photosensitivity according to the wavelength of the detected ray, at a temperature of 25° C. Thus, it is worth noting that such a silicon photodiode has a photosensitivity in the magnitude of 0.17 A/W for a wavelength in the magnitude of 370 nm, corresponding as a reminder substantially to the length of the main beam FP, and hence of the second reference beam FR, after passing through the aforementioned optical band-pass filter 11.

For the second photodetector means 15 to be sensitive to the second reference beam FR, the system 1 comprises, in a channel for guiding the second reference beam FR placed between the optical splitter 13 and the second photodetector means 15, a low-pass filter 151 and a waveguide 152.

The optical low-pass filter 151 has a low-wavelength cutoff substantially lower than the wavelength of the second reference beam FR, which as a reminder, is in the magnitude of 370 nm.

For example, the optical low-pass filter 151 has the following optical features:
transmission percentage in the magnitude of 40%±5% for the wavelength range ranging between 360 and 380 nm;
transmission percentage lower than 1% for the wavelength range ranging between 405 and 790 nm; and
transmission percentage in the magnitude of 0.2% for the wavelength range ranging between 425 and 790 nm.

The waveguide 152 is preferably achieved in the form of a guiding cone or optical cone, for example polymethyl methacrylate (PMMA), in order to channel the second reference beam FR filtered by the optical low-pass filter 151 in the direction of the second photodetector means 15.

In the embodiment of FIG. 3 reflecting mirrors 144 and 154 are arranged at 45° respectively after the objective lens 143 on the channel for guiding the fluorescence ray RF and after the optical splitter 13 on the channel for guiding the second reference beam FR, in order to be able to arrange the two photodetector means 14, 15 underneath the diode 10.

In other non illustrated embodiments, other optical members may be incorporated such as for example additional lenses.

The second part of the following description relates to the processing part of the signal of the system 1 in accordance with the invention which allows to analyze the signals from the two photodetector means 14, 15 and to control the diode 10 in order to carry out a detection by fluorometry of the analyte in the sample E, with the advantage of obtaining a very satisfactory signal-to-noise ratio.

Figure 8:
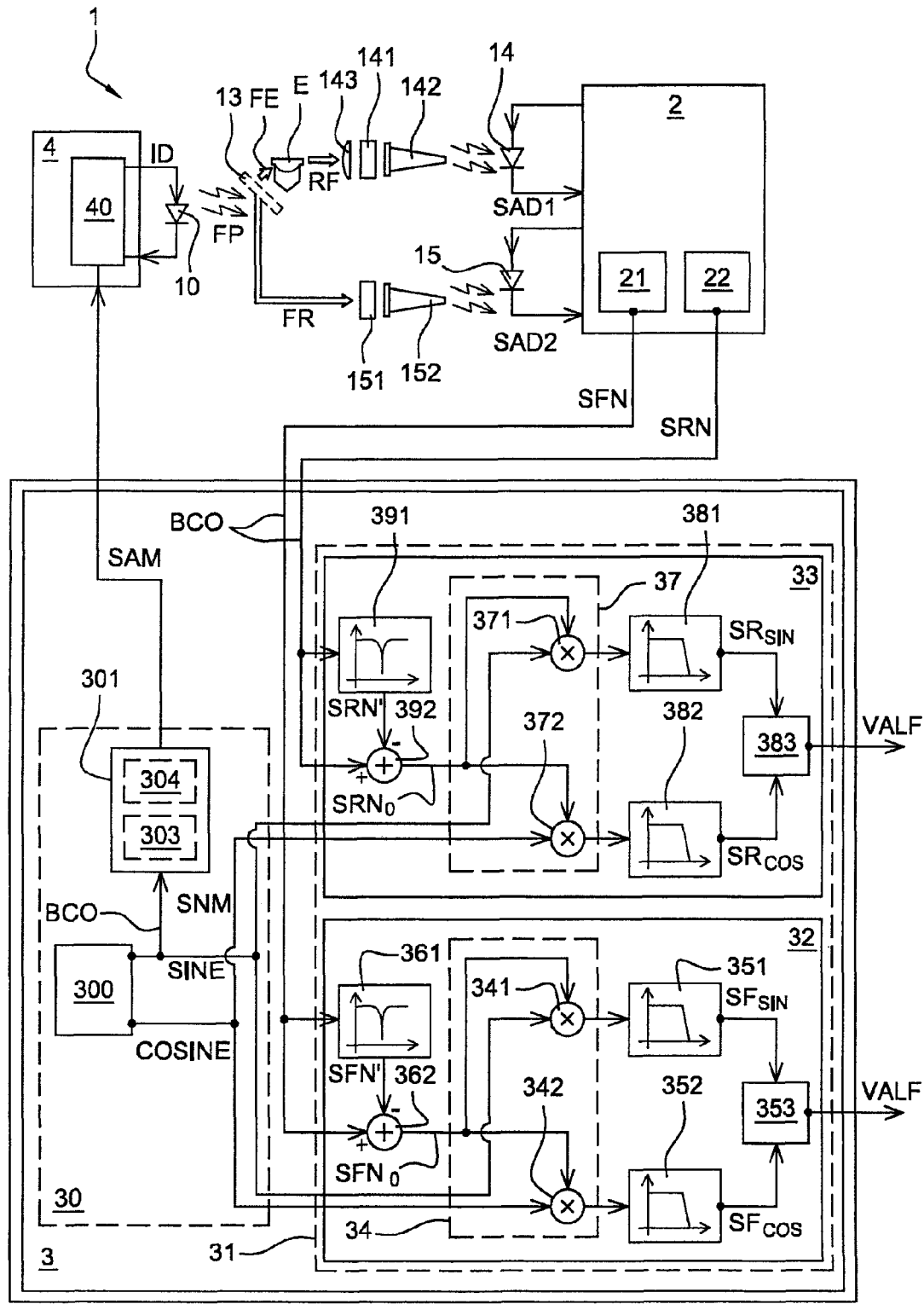
FIG. 8 is a schematic view of a system in accordance with the invention illustrating its signal processing portion, according to a first configuration.

FIG. 8 schematically illustrates a system 1 in accordance with the invention fitted with its signal processing part, according to a first configuration.

This signal processing part comprises three main boards, namely:
a preamplification board 2 connected to the two photodetector means 14, 15;
a digital signal process board 3 arranged at the output of the preamplification board 2 to calculate the quantity of analytes in the sample; and
a driver board 4 of the diode 10 or "LED Driver Board" arranged at the output of the digital signal process board 3 and driving the diode 10 in current.

The preamplification board 2 comprises:
a first analog/digital conversion means 21 connected to the first photodetector means 14 for converting the first analog detection signal SAD1 into a first digital so-called fluorescence signal SFN.
a second analog/digital conversion means 22 connected to the second photodetector means 15 for converting the second analog detection signal SAD2 into a second digital so-called reference signal SRN.

Figure 12:
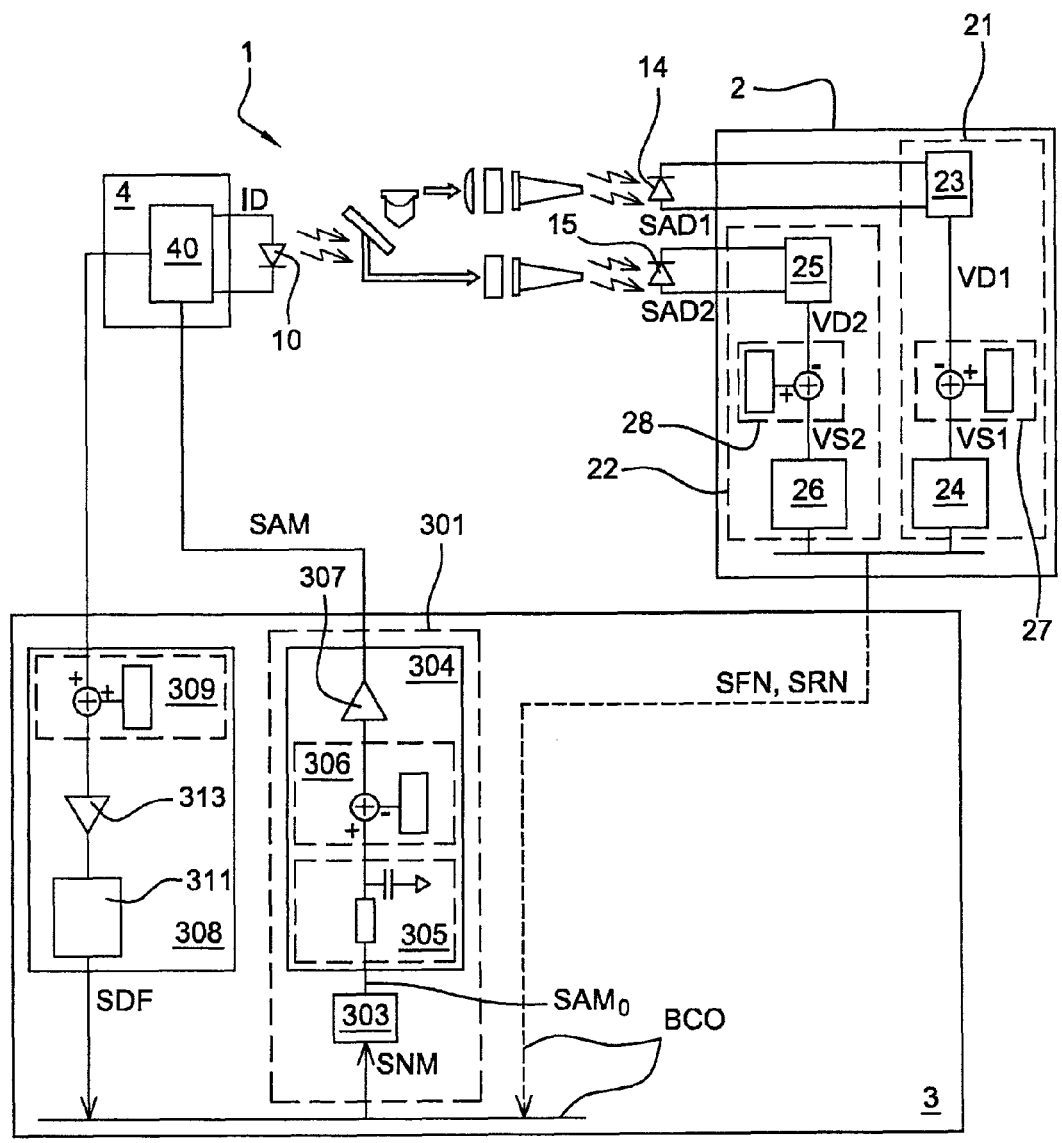
FIG. 12 is a schematic view of a system in accordance with the invention illustrating its signal processing portion, according to a second configuration corresponding to an improvement of the first configuration.

FIG. 12 pertaining to a second configuration of the system 1, illustrates the preamplification board 2 in a more complete and detailed manner.

As is visible on this FIG. 12, the first analog/digital conversion means 21 comprises:
a first current/voltage converter 23 for converting the first analog detection signal SAD1 (intensity in amperes) into a first detection voltage VD1 (in volts), with a conversion of type VD1=SAD1·RD1, where RD1 corresponds to a first resistance in Ohms used for the current SAD1/voltage VD1 conversion; and
a first analog/digital converter 24 at the output of the first current/voltage converter 23 for converting the first detection voltage VD1 into the first digital so-called fluorescence signal SFN.

Similarly, the second analog/digital conversion means 22 comprises:
a second current/voltage converter 25 for converting the second analog detection signal SAD2 (intensity in amperes) into a second detection voltage VD2 (in volts), with a conversion of type VD2=SAD2·RD2, where RD2 corresponds to a second resistance in Ohms used for the current SAD2/voltage VD2 conversion; and
a second analog/digital converter 26 at the output of the second current/voltage converter 25 for converting the second detection voltage VD2 into the second digital so-called reference signal SRN.

In an improvement illustrated on FIG. 12, the first analog/digital conversion means 21 further comprises a first subtracter 27 which subtracts from the first detection voltage VD1 an offset voltage $V_{OFF}$, in order to output a voltage VS1=$V_{OFF}$–VD1, this first subtracter 27 being interposed between the first current/voltage converter 23 and the first analog/digital converter 24.

Similarly, the second analog/digital conversion means 22 further comprises a second subtracter 28 which subtracts from the second detection voltage VD2 the same offset voltage Voff, in order to output a voltage VS2=$V_{OFF}$–VD2, this second subtracter 28 being interposed between the second current/voltage converter 25 and the second analog/digital converter 26.

The introduction of an offset voltage $V_{OFF}$ allows to use all the dynamic for inputting digital/analog converters 24, 26 by injecting in the latter voltages suitable for their performance.

As illustrated on FIG. 8, the digital signal process board comprises a module for generating modulation/demodulation signals 30, which comprises:
 a generator 300 outputting a sinusoidal carrier signal SNM at a predefined carrier frequency $f_0$, which is fixed for the rest of the description at 2 kHz; and
 an analog output module 301 arranged at the output of the generator 30.

Figure 9:
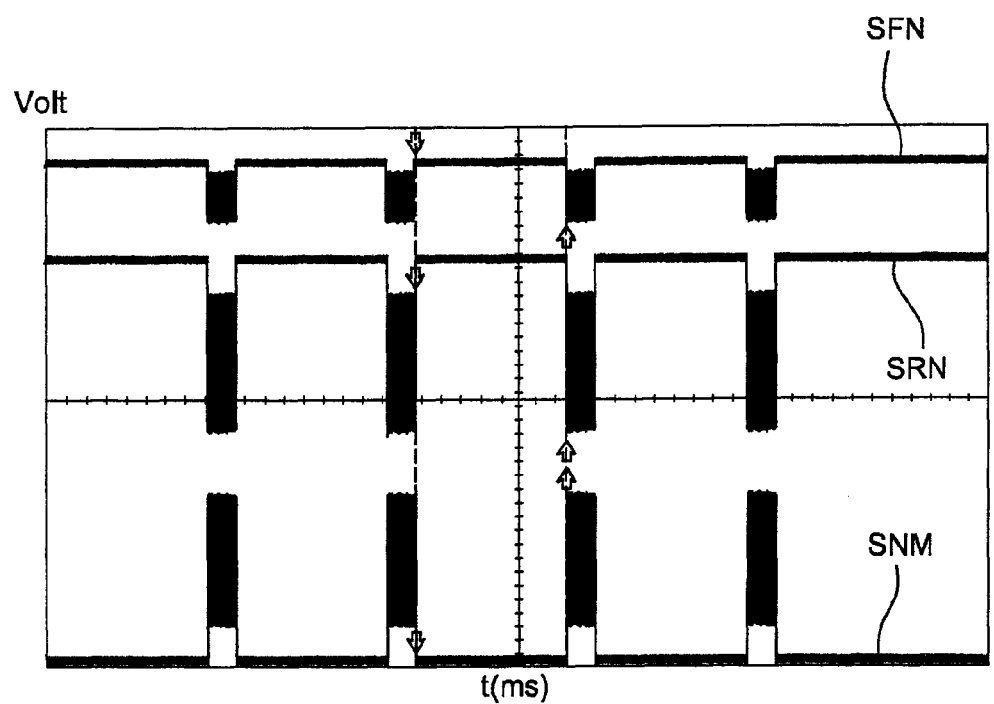
FIG. 9 is a graph illustrating the variation curves according to the time of the sinusoidal carrier signal SNM, of the first digital fluorescence signal SRI and the second digital reference signal SRN, these signals come in the form of four sinusoidal periodic iterations.

With reference to FIG. 9, the sinusoidal carrier signal SNM is transmitted in digital data packets of 16 bits, and comes in the form of a set of several periodic sinusoidal iterations.

Figure 10:
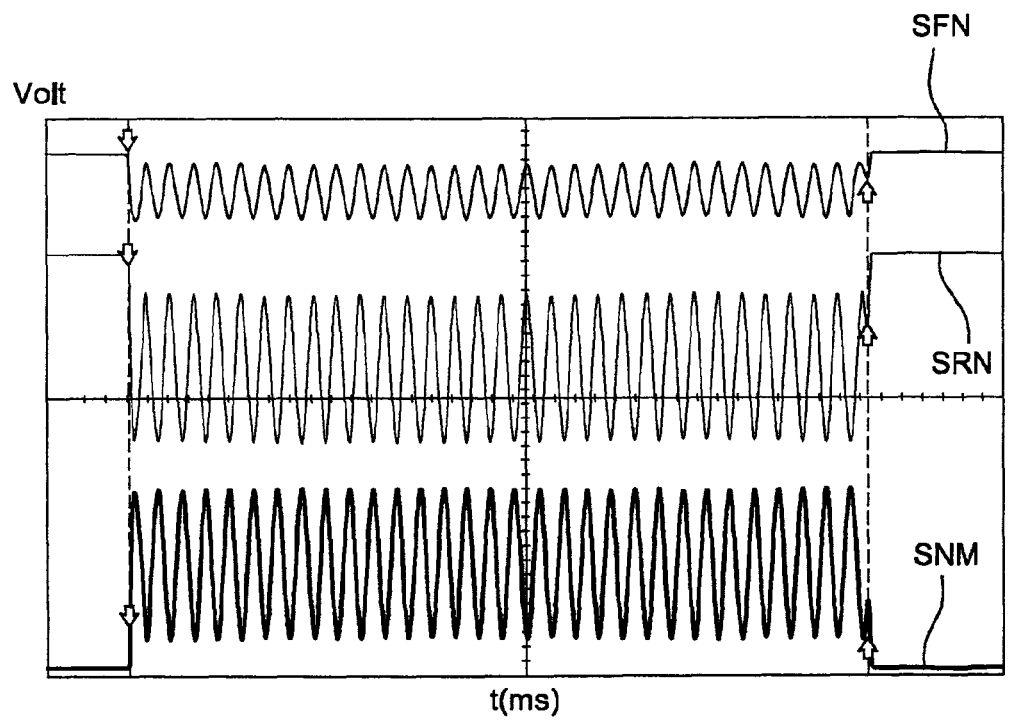
FIG. 10 is a graph illustrating an iteration for the three curves of FIG. 9.

In the example of FIGS. 9 and 10 (FIG. 10 illustrating one of the five iterations of the three curves of FIG. 9), the number of iterations is four and each iteration is formed of thirty one sinusoidal oscillations. Each sinusoidal oscillation (otherwise a unique period of the sinusoidal signal) is constructed with forty sampling points each spaced apart by 12.5 µs (namely 0.0125 ms).

Thus, the period of the sinusoidal signal inside an iteration is of 500 µs (namely 0.5 ms, corresponding to forty times 0.0125 ms). Consequently, each sinusoidal iteration lasts 15.5 ms, equivalent to thirty one times the period of 0.5 ms, due to the thirty one sinusoidal oscillations in an iteration.

The time difference between two consecutive iterations, in other words between the end of an iteration and the beginning of an iteration, is of 80 ms, much higher than the period of sinusoidal oscillations (0.5 ms) and the duration of an iteration (15.5 ms). Thus, the periodicity of the iterations is of 95.5 ms and in total, a set of four iterations generally lasts 302 ms between the first and last iterations.

The generator 300 also emits two digital demodulation signals at this same carrier frequency $f_0$, namely:
 a digital demodulation signal SINE at the carrier frequency f0 and in phase with the sinusoidal carrier signal SNM, this digital demodulation signal SINE being identical to the sinusoidal carrier signal SNM; and
 a digital demodulation signal COSINE at the carrier frequency $f_0$ and in phase quadrature with respect to the sinusoidal carrier signal SNM.

For this, the generator 300 integrates a phase shifter at 90° for generating the digital demodulation signal COSINE.

The analog output module 301, at the output of the generator 300, successively comprises:
 a digital/analog conversion means 303 for converting the sinusoidal carrier signal SNM, before filtering, into an initial analog modulation signal $SAM_0$ at the carrier frequency $f_0$; and
 at the output of the digital/analog conversion means 303, an analog processing module 304 which analogically processes the initial analog modulation signal $SAM_0$ for outputting an analog modulation signal SAM "or LED signal" at the carrier frequency $f_0$, this analog modulation signal SAM forming an analog drive signal of the diode 10.

As illustrated on FIG. 12, this analog processing module 304 successively comprises:
 a low-pass filter 305 of RC filter type;
 at the output of the low-pass filter 305, a subtracter 306 which subtracts from the output voltage of the filter 305 a so-called offset voltage Txoffset, which allows to maintain the diode 10 switched off when the initial analog modulation signal $SAM_0$ is zero, with for example Txoffset=0.012 V; and
 at the output of the subtracter 306, an amplifier 307 of predefined gain, and which outputs the analog modulation signal SAM.

Before going on to describe the digital signal process board 3, it is worth noting that the driver board 4 comprises an amplitude modulator connected to the digital/analog conversion means 303 and to the diode 10 for modulating in amplitude the main beam FP at the carrier frequency $f_0$, by applying the analog modulation signal SAM on the diode 10.

The driver board 4 more particularly comprises a voltage/current converter 40 for converting the analog modulation signal SAM into a drive current ID of the diode 10 via a resistance RD in Ohms. The real voltage VD measured at the terminals of the resistance RD corresponds to a sinusoidal feedback signal of the diode 10 (LED Feedback Signal) and satisfies the relationship VD=ID·RD.

Thus, the driver board 4 drives in voltage and hence in intensity the diode 10 such that it emits a main beam FP composed of several flashes regularly spaced over time, each flash being modulated at the carrier frequency $f_0$, in other words exhibits a sinusoidal component at the carrier frequency $f_0$.

In the example of FIG. 12, the digital signal process board 3 further comprises a retroactive control module 308 that receives in input the measured voltage VD (sinusoidal feedback signal) coming from the driver board 4 in order to determine the error or the shift between this voltage VD measured at the terminals of the resistance RD and the analog modulation signal SAM which drives the diode 10, for a servo-control by return loop of the drive current ID of the diode 10.

This retroactive control module 308 successively comprises:
 at the output of the driver board 4, a summer 309 which sums up the measured voltage VD and a so-called offset voltage RXoffset, which allows to compensate for the incoming negative voltage VD when the initial analog modulation signal $SAM_0$ is zero, with for example Rxoffset=0.038 V;
 at the output of the summer 309, an amplifier 313 of predefined gain; and
 at the output of the amplifier 313, an analog/digital converter 311 which outputs a digital feedback signal SFD.

A first purpose of this retroactive control module 308 is to be able to adjust the amplitude and the zero (typically called "offset") of the drive current ID (ID=VD/RD), so that this drive current ID corresponds to the required sinusoidal signal.

A second purpose of this retroactive control module 308 is to be able to control, with each signal iteration, the shift between the drive current ID and the analog modulation signal SAM, so as to generate alerts if a shift or error threshold is exceeded.

Due to the modulation of the main beam FP, the two analog detection signals SAD1, SAD2, measured at the terminals of the two photodetectors 14, 15, also each come in the form of a set of several periodic sinusoidal iterations at the carrier frequency $f_0$.

Thus, and as illustrated on FIGS. 9 and 10, the first digital fluorescence signal SFN (or "Fluo signal") and the second digital reference signal SRN (or "Ref Signal"), at the output of the preamplification board 2, each come in the form of a set of several periodic sinusoidal iterations, substantially having the same temporal and frequential features as the sinusoidal carrier signal SNM.

The digital signal process board 3 comprises a main signal acquisition/processing module 31 arranged at the output of the generator 300 and the preamplification board 2. This digital signal process board 3 comprises a first module for acquiring/processing 32 the digital fluorescence signal SFN (or "Fluo Signal") and a second module for acquiring/processing 33 the second digital reference signal SRN (or "Ref Signal").

From a communication aspect, the digital signal process board 3 uses for the transmission of the sinusoidal carrier signal SNM and the reception/acquisition, of the first digital fluorescence signal SFN and the second digital reference signal SRN, a digital communication bus BCO such as for example of SPI type (Serial Peripheral Interface Bus) with 32 bits, capable of receiving and emitting 32 bits at the same time.

Figure 11:
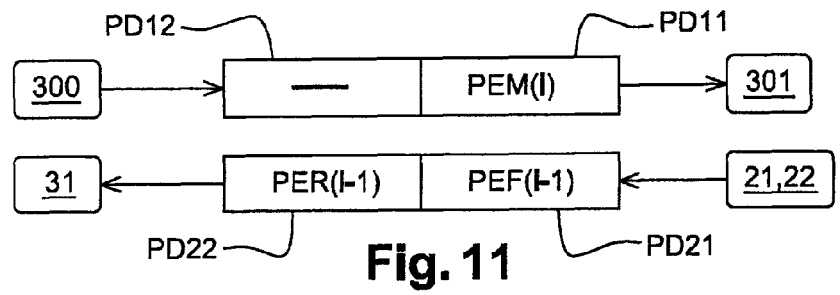
FIG. 11 is a schematic view of two frames transporting the digital data for the system in accordance with the invention.

With reference to FIG. 11, the generator 300 of the digital signal process board 3 emits at a regular interval a sampling point PEM(i) (i being an integer) for the sinusoidal carrier signal SNM within a data packet PD11 of 16 bits of the frame of 32 bits, the other data packet PD12 of 16 bits being unused. As a reminder, the time difference between two successive sampling points PEM(i−1) and PEM(i) is of 12.5 μs (namely 0.0125 ms), which corresponds to a time difference between two successive frames of 12.5 μs.

With reference to FIG. 11, each time a sampling point PEM(i) is transmitted for the sinusoidal carrier signal SNM, the digital signal process board 3, and more particularly its main signal acquisition/processing module 31, receives a sampling point PEM(i−1) for the first digital fluorescence signal SFN and a sampling point PEM(i−1) for the second digital reference signal SRN; the sampling points PEM(i−1) and PER (i−1) being the responses to the previously emitted sampling point PEM(i−1) for the sinusoidal carrier signal SNM. The sampling point PEF(i−1) and PER(i−1) are transmitted and received in two respective data packets PD21, PD22 of 16 bits of the frame of 32 bits.

Thus, the time interval between two sampling points PEM(i) for the sinusoidal carrier signal SNM (12.5 μs) corresponds to the same acquisition time interval between the sampling points PEF(i) and PER(i).

Thanks to the phase and quadrature coherent demodulation process implemented by the main signal acquisition/processing module 31 and described later, all the phase shifts possibly introduced by the system not affecting the signal analysis for extracting a quantification value of the analyte in the sample E; the origin of such phase shifts may be in response times between the drive current ID and the emission of the main beam FP, delays introduced along optical paths of the beams FP, FE, FR, RF, response times between the detection of the fluorescence ray RF by the first photodiode 14 and the generation of the first analog detection signal SAD1, response times between the detection of the second reference beam FR by the second photodiode 15 and the generation of the second analog detection signal SAD2, the phase inversion introduced by the first subtracter 27 of the first analog/digital conversion means 21 and the phase inversion introduced by the second subtracter 28 of the second analog/digital conversion means 22 (see FIG. 12), trans-impedance amplification delays introduced by parasitic capacitors.

It is particularly interesting to generate a sinusoidal carrier signal SNM in the form of a set of several periodic sinusoidal iterations.

In fact, it is possible to use the first iteration only to check if the two analog detection signals SAD1, SAD2 are above predefined minimum threshold, for example fixed at −7V and +8V. If the first detection signal SAD1 is below the corresponding minimum threshold, a return loop is provided for reducing the analog modulation signal SAM, particularly in the magnitude of three times with respect to the initial signal.

Thus, a correction coefficient is applied upstream on the module of the first detection signal SAD1, for each iteration, in order to compensate for a decrease of the first energizing beam FE. The purpose of such a return loop is to prevent an incorrect reading due to electronic channel saturations, and also to extend the fluorescent reading range, such that even high concentrations of 4-MU may be detected.

The three other iterations are used to extract the values of the modules of the first digital fluorescence signal SFN and the second digital reference signal SRN, for each iteration.

Inside each of these three iterations, the last sinusoidal oscillation is used to check the voltage VD, also called the sinusoidal feedback signal of the diode 10 (Led Feedback Signal) which corresponds as a reminder to the real voltage measured at the terminals of the diode 10.

For the sake of precision, and in accordance with the amplitude modulation principle, the module of the first digital fluorescence signal SFN corresponds to the envelop of the sinusoidal part (inside a sinusoidal iteration) of the first digital fluorescence signal SFN, and the module of the second digital reference signal SRN corresponds to the envelop of the sinusoidal part (inside a sinusoidal iteration) of the second digital reference signal SRN.

In the example illustrated on FIGS. 9 and 10, the digital fluorescence SFN and reference SRN signals are modulated signals and the respective modules of these two signals substantially correspond to half the voltage amplitude Vpp of the sinusoidal part of the corresponding signal.

In order to detect a possible defect or a possible failure in the diode 10 or optical devices 11, 12, 13 illustrated on FIGS. 2 and 3, the digital signal process board 3 automatically checks, at the end of each iteration, that the module of the second digital reference signal SRN ranges within a predefined operating range, in other words between two predefined safety thresholds.

The rest of the description specifically relates to the main signal acquisition/processing module 31, which allows to implement a phase and quadrature coherent demodulation process.

The main signal acquisition/processing module 31 includes, as a reminder:

a first acquisition/processing module 32 connected to the generator 300 and to the first analog/digital conversion means 21 of the preamplification board 2, for acquiring and processing the first digital fluorescence signal SFN; and a second acquisition/processing module 33 connected to the generator 300 and to the second analog/digital conversion means 22 of the preamplification board 2, for acquiring and processing the second digital reference signal SRN.

The first acquisition/processing module 32 comprises a first demodulation means 34 designed to demodulate the first digital fluorescence signal SFN, and comprising:

- a first multiplier 341 by the digital demodulation signal SINE in phase, this first multiplier 341 being followed by a first low-pass filter 351 at a cutoff frequency $f_c$ lower than the carrier frequency $f_0$ (for example $f_c$=110 Hz), in order to output a first so-called in phase $SF_{SIN}$ demodulated fluorescence signal; and
- a second multiplier 342 by the digital demodulation signal COSINE in phase quadrature, this second multiplier 342 being followed by a second low-pass filter 352 at the same cut-off frequency $f_c$, in order to output a first so-called phase quadrature $SF_{COS}$ demodulated fluorescence signal.

The first acquisition/processing module 32 further comprises, at the output of the first and second low-pass filters 351, 352, a means 353 for calculating a first so-called fluorescence VALE value characteristic of the amplitude of the fluorescence ray RF, corresponding to the module of the first digital fluorescence signal SFN and thus to the module of the sum of the first in phase demodulated fluorescence signal $SF_{SIN}$ and the first phase quadrature demodulated fluorescence signal $SF_{COS}$.

More particularly, the first fluorescence value VALF is calculated according to the following equation: VALF= $(SF_{SIN}^2+SF_{COS}^2)^{1/2}$.

The first acquisition/processing module 32 also comprises, at the input of the first and second multipliers 341, 342:

- a notch filter 361 centered on the carrier frequency $f_0$ in order to filter the first digital fluorescence signal SFN and output a first filtered intermediate signal SFN'; and
- a subtracter 362 performing the subtraction of the first digital fluorescence signal SFN and the first filtered intermediate signal SFN', in order to generate a first filtered fluorescence signal $SFN_0$=SFN−SFN', this first filtered fluorescence signal $SFN_0$ being injected in the first and second multipliers 341, 342.

The second acquisition/processing module 33 comprises a second demodulation means 37 designed for demodulating the second digital reference signal SRN, and comprising:

- a first multiplier 371 by the digital demodulation signal SINE in phase, this first multiplier 371 being followed by a first low-pass filter 381 at the cutoff frequency $f_c$ lower than the carrier frequency $f_0$ in order to output a second so-called in phase demodulated reference signal $SR_{SIN}$; and
- a second multiplier 372 by the digital demodulation signal COSINE in phase quadrature, this second multiplier 372 being followed by a second low-pass filter 372 at the same cut-off frequency $f_c$, in order to output a second so-called phase quadrature demodulated fluorescence signal $SF_{COS}$.

The second acquisition/processing module 33 further comprises at the output of the first and second low-pass filters 381, 382, a means 383 for calculating a second so-called reference value VALR characteristic of the amplitude of the reference beam FR, corresponding to the module of the second digital reference signal SRN and thus to the module of the sum of the second in phase demodulated reference signal $SR_{SIN}$ and the second phase quadrature demodulated reference signal $SR_{COS}$.

More particularly, the second reference value VALR is calculated according to the following equation: VALR= $(SR_{SIN}^2+SR_{COS}^2)^{1/2}$.

The second acquisition/processing module 33 also comprises, at the input of the first and second multipliers 371, 372:

- a notch filter 391 centered on the carrier frequency $f_0$ in order to filter the second digital reference signal SRN and output a second filtered intermediate signal SRN'; and
- a subtracter 392 performing the subtraction of the second digital reference signal SRN and the second filtered intermediate signal SRN', in order to generate a second filtered reference signal $SRN_0$=SRN−SRN', this second filtered reference signal $SRN_0$ being injected in the first and second multipliers 371, 372.

The rest of the description relates to the calculations implemented for determining the fluorescence of the sample E by expressing it in the form of a relative fluorescence unit (RFU), the relative fluorescence unit being defined as the ratio between the intensity of fluorescence and the intensity of excitation.

The RFU values are usually adjusted for a required scale of values, determined by a prior calibration process.

In the case of the present system 1, for a given concentration "x" of the 4-MU contained in the sample E during measurement by fluorometry, the calibrated RFU value is calculated as follows:

$$RFU_{cal}(x)=(Fx \cdot g_{FLUO})/(Rx \cdot g_{REF}), \text{where}$$

Fx is a raw value in mV of the fluorescence signal detected in the first photodetector, which corresponds within the scope of the invention, to the first fluorescence value VALF (digital data) from the demodulation process implemented in the digital signal process board 3;

Rx is a raw value in mV of the reference signal detected in the second photodetector, which corresponds within the scope of the invention, to the second reference value VALR (digital data) from the demodulation process implemented in the digital signal process board 3; and $g_{FLUO}$ and $g_{REF}$ are gain parameters adjusted during the optical calibration of the system 1.

The calibration process is carried out by a prior analysis by fluorometry, of a liquid solution of reference having a known concentration $C_{REF}$ of the 4-MU and providing a given value of $RFU_{REF}$, with for example $C_{REF}$=6410 nM and $RFU_{REF}$=3144 with a certain precision interval. The gain parameters $g_{FLUO}$ and $g_{REF}$ are established during the analysis in order to obtain at the output a RFU in the magnitude of $RFU_{REF}$.

Figure 13:
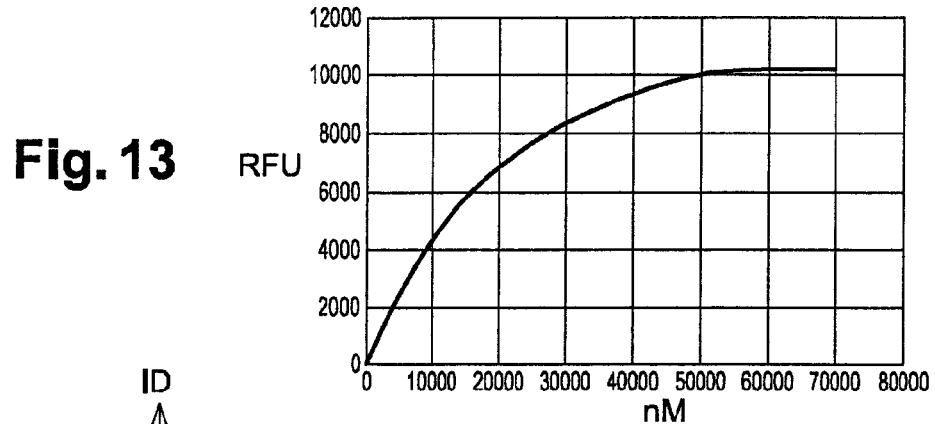
FIG. 13 is a graph illustrating the variation curve of RFU according to the concentration in 4-MU in the sample.

Within the scope of an immunological test, the concentration of the 4-MU is situated in the 40 nM-40000 nM range. FIG. 13 illustrates the variation of the RFU according to the concentration in 4-MU, with RFU non linear function of the concentration in 4-MU. In order to obtain such a curve with a system 1 in accordance with the invention, it is provided to apply at the output of the digital signal process board 3 a conversion factor $F_{CONV}$, in this instance, a polynomial function of the concentration in 4-MU, so that the RFU measured by the system 1 coincides with the curve illustrated in FIG. 13 and thus obtain the required curve shape. This conversion factor $F_{CONV}$ is established by following an analysis protocol by fluorometry including several variation factors (different solutions of 4-MU and different optical instruments) in order to ensure the reliability and repeatability of the measurement.

The detail of the calculations is described hereinafter.

First, the drive current ID(t) of the diode 10 is established, from the conversion of the analog modulation signal SAM. For a sinusoidal pulse, the drive current ID(t) (or diode current) satisfies the following equation (E1):

$$ID(t)=[A+B \cdot \sin(2\pi f_0 t)] \cdot rect_T(t), \text{ namely}$$

$$ID(t)=[A+B \cdot \cos(2\pi f_0 t - \pi/2)] \cdot rect_T(t) \quad (E1)$$

Where
$f_0$=2 KHz (carrier frequency),
T=15.5 ms (duration of a sinusoidal pulse),
A corresponds to the offset intensity (shift with respect to zero), which may take the value of 15 mA, and
B corresponds to the half-amplitude of the drive current, which may take the value of 10 mA.

Figure 14:
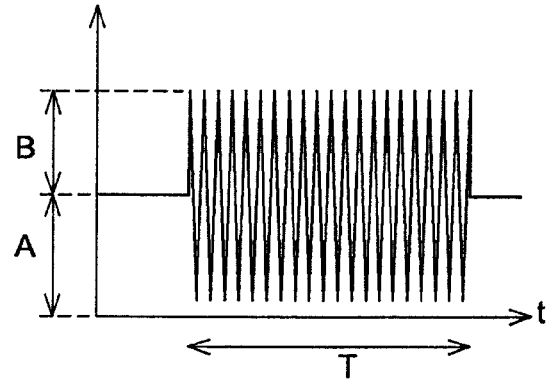
FIG. 14 is a graph illustrating the variation curve of the drive current ID(t) according to the time t for a pulse.

FIG. 14 illustrates this drive current ID(t) according to time t for a pulse.

In the frequential field, this equation (E1) is translated by the following equation (E2):

$$ID(f)=A \cdot T \cdot \sin c(fT) + B \cdot T/2 \cdot (e^{-j\pi/2} \cdot \sin c[(f-f_0)T] + e^{j\pi/2} \cdot \sin c[(f+f_0)T]) \quad (E2)$$

Figure 15:
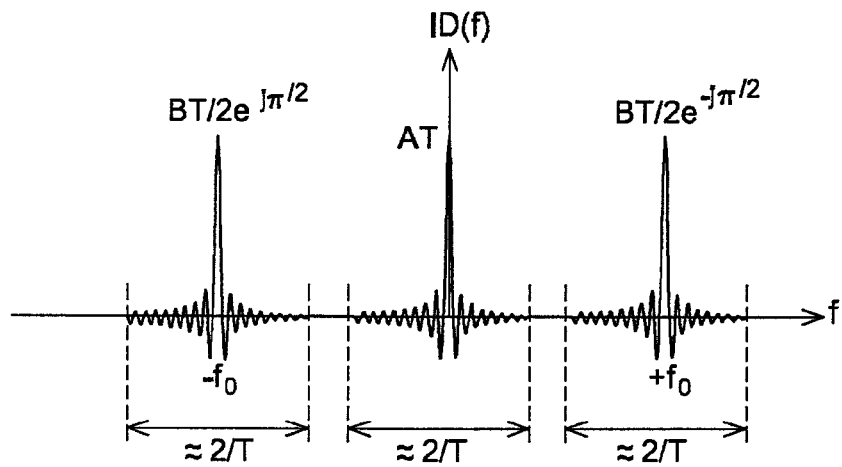
FIG. 15 is a graph illustrating the variation curve of the drive current ID(t) according to the frequency f.

FIG. 15 illustrates ID(f) according to the frequency f.

Second, the drive current ID(t) (carrier signal from the modulation process at the carrier frequency $f_0$) is converted into the main beam FP at a given wavelength, in this instance around 370 nm, before being split into a first energizing beam FE and a second reference beam FR. The first energizing beam FE excites the sample and the molecules of 4-MU, which in return emit a fluorescence ray RF detected by the first photodetector 14; this photodetection being translated by a first analog detection signal SAD1 at the terminals of the first photodetector 14.

It is established the following equation (E3) which translates the passage of the drive current ID(t) to the first analog detection signal SAD1(t), signal at the output of the first photodetector 14 and at the input of the first analog/digital conversion means 21 or the first analog/digital converter 24:

$$SAD1(t)=z(t) \cdot ID(t), \text{ namely}$$

$$SAD1(t)=K \cdot [A+B \cdot \cos(2\pi f_0 t - \pi/2 + \Delta)] \cdot rect_T(t), \text{ namely}$$

$$SAD1(t)=K \cdot A \cdot rect_T(t) + [K \cdot B \cdot \cos(2\pi f_0 t + \partial)] \cdot rect_T(t) \quad (E3)$$

where
z(t) is the amplification signal translating the emission of the fluorescence ray RF, and which is considered as constant and equal to the constant K;
$\partial = \Delta - \pi/2$, with $\Delta$ corresponding to a phase shift introduced by the system between the diode 10 and the first photodetector 14.

Figure 16:
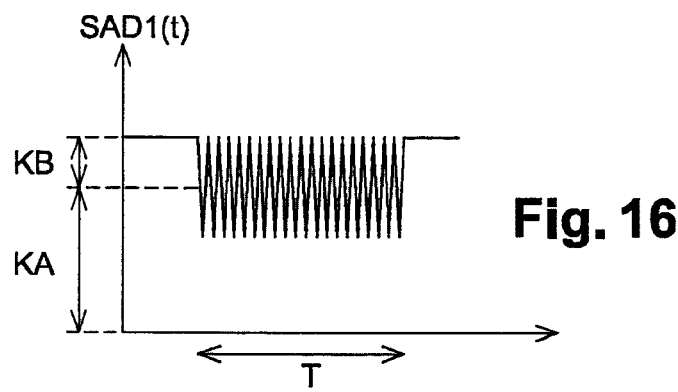
FIG. 16 is a graph illustrating the variation curve of the first analog detection signal SAD1(t) according to the time t for a pulse.

FIG. 16 illustrates this first analog detection signal SAD1 (t) according to time t for a pulse.

Third, the analog detection signal SAD1(t) is converted into a digital signal to give the first digital fluorescence signal SFN, after passage in the first analog/digital conversion means 21. In the frequential field, the following equation (E4) is thus obtained:

$$SFN(f)=K \cdot A \cdot T \cdot \sin c(fT) + K \cdot B \cdot T/2 \cdot (e^{j\partial} \cdot \sin c[(f-f_0)T] + e^{-j\partial} \cdot \sin c[(f+f_0)T]), \text{ namely}$$

$$SFN(f)=Y(f)=K \cdot A \cdot T \cdot \sin c(fT) + K \cdot B \cdot T/2 \cdot (e^{j\partial} \cdot \sin c[(f-f_0)T] + e^{-j\partial} \cdot \sin c[(f+f_0)T]) \quad (E4)$$

FIG. 17 illustrates SFN(t) according to frequency f.

The first digital fluorescence signal SFN is then acquired and processed by the digital signal process board 3, and more particularly by the main signal acquisition/processing module 31, according to the following steps of the demodulation process.

In a first step of the demodulation process, the first digital fluorescence signal SFN(f) passes through a band-pass filter composed of the notch filter 361 associated with the subtracter 362.

The notch filter 361 translates into a function $H_{notch}(f)$ centered on the carrier frequency $f_o$ with a low-frequency cutoff $f_1=|f_o|-$fdec and a high-frequency cutoff $f_2=|f_o|+$fdec, where fdec can be set at 100 Hz, such that the frequential width $\Delta f_{notch}$ of the notch is $\Delta f_{notch}=2 \cdot f_{dec}=200$ Hz. FIG. 18 illustrates the function $H_{Notch}(f)$ according to the frequency f.

The first filtered intermediate signal SFN'(f) hence satisfies the equation $SFN'(f)=H_{Notch}(f) \cdot SFN(f)$.

Thus, the band-pass filter composed of the notch filter 361 associated with the subtracter 362, translates by a function $H_{BP}(f)=1-H_{Notch}(f)$, which is applied to the first digital fluorescence signal SFN(f).

The first filtered fluorescence signal $SFN_0(f)=SFN(f)-SFN'(f)$, thus satisfies the following equation (E5):

$$SFN_0(f)=H_{BP}(f) \cdot SFN(f)=(1-H_{Notch}(f)) \cdot SFN(f), \text{ namely}$$

$$SFN_0(f)=K \cdot B \cdot T/2 \cdot (e^{j\partial} \cdot \sin c[(f-f_o)T] + e^{-j\partial} \cdot \sin c[(f+f_o)T]) \quad (E5)$$

FIG. 19 illustrates $SFN_0(f)$ according to the frequency f.

In the temporal field, this equation (E5) translates by the following equation (E6):

$$SFN_0(t)=[K \cdot B \cdot \cos(2\pi f_o t + \partial)] \cdot rect_T(t), \text{ thus}$$

$$SFN_0(t)=K \cdot B \cdot rect_T(t) \cdot \cos(\partial) \cdot \cos(2\pi f_o t) - K \cdot B \cdot rect_T(t) \cdot \sin(\partial) \cdot \sin(2\pi f_o t), \text{ namely}$$

$$SFN_0(t)=Kc(t) \cdot \cos(2\pi f_o t) - Ks(t) \cdot \sin(2\pi f_o t)$$

$$\text{avec } Kc(t)=K \cdot B \cdot rect_T(t)\cos(\partial) \text{ et } Ks(t)=K \cdot B \cdot rect_T(t) \cdot \sin(\partial) \quad (E6)$$

In a second step of the demodulation process, the first filtered fluorescence signal $SFN_0$ passes by the two multipliers 341, 342 so as to be multiplied by the digital demodulation signals SINE and COSINE. For the description of this step, reference will be usefully made to FIG. 20 which specifically illustrates the two multipliers 341, 342, as well as the low-pass filters 351, 352 and the calculation means 353 that follows.

The $SFN_0(t)$ signal is multiplied, on the one hand, in the first multiplier 341 by the digital demodulation signal SINE so as to generate at the output a first in phase intermediate demodulated signal $SF_{SIN}(t)$ and on the other hand, in the second multiplier 342 by the digital demodulation signal COSINE so as to generate at the output a first phase quadrature intermediate demodulated signal $SF_{COS}'(t)$.

The digital demodulation signals SINE and COSINE come in the following temporal forms:

$$SINE(t)=K_{sin} \cdot \sin(2\pi f_o t)=2 \cdot \sin(2\pi f_o t), \text{ and}$$

$$COSINE(t)=K_{cos} \cdot \cos(2\pi f_o t)=2 \cdot \cos(2\pi f_o t)$$

Where $K_{sin}$ and $K_{cos}$ correspond to the amplitudes of the signals and are set at the value of 2.

The in-phase intermediate demodulated signal $SF_{SIN}(t)$ and the phase quadrature intermediate demodulated signal $SF_{COS}'(t)$ satisfy the following equations (E7) and (E8), in the temporal field:

$$SF_{SIN}'(t)=[Kc(t)\cdot\cos(2\pi f_o t)-Ks(t)\cdot\sin(2\pi f_o t)]\cdot 2\sin(2\pi f_o t), \text{ namely}$$

$$SF_{SIN}'(t)=2\cdot[\tfrac{1}{2}\cdot Ks(t)-\tfrac{1}{2}\cdot Kc(t)\cdot\cos(2\pi 2f_o t)-\tfrac{1}{2}\cdot Ks(t)\cdot\sin(2\pi 2f_o t)], \text{ namely}$$

$$SF_{SIN}'(t)=Ks(t)-Kc(t)\cdot\cos(2\pi 2f_o t)-Ks(t)\cdot\sin(2\pi 2f_o t) \quad (E7)$$

$$SF_{COS}'(t)=[Kc(t)\cdot\cos(2\pi f_o t)-Ks(t)\cdot\sin(2\pi f_o t)]\cdot 2\cos(2\pi f_o t), \text{ namely}$$

$$SF_{COS}'(t)=2\cdot[\tfrac{1}{2}\cdot Kc(t)+\tfrac{1}{2}\cdot Kc(t)\cdot\cos(2\pi 2f_o t)-\tfrac{1}{2}\cdot Ks(t)\cdot\sin(2\pi 2f_o t)], \text{ namely}$$

$$SF_{COS}'(t)=Kc(t)+Kc(t)\cdot\cos(2\pi 2f_o t)-Ks(t)\cdot\sin(2\pi 2f_o t) \quad (E8)$$

In the frequential field, these equations (E7) and (E8) translate into the following equations (E9) and (E10):

$$SF_{SIN}'(f)=[K\cdot B\cdot T\cdot\sin(\Theta)]\cdot\sin c(fT)-[(K\cdot B\cdot T\cdot\cos(\Theta))/2]\cdot(\sin c[(f-2f_o)T]+\sin c[(f+2f_o)T])-[(K\cdot B\cdot T\cdot\sin(\Theta))/2]\cdot(e^{-j\pi/2}\cdot\sin c[(f-2f_o)T]+e^{j\pi/2}\cdot\sin c[(f+2f_o)T]) \quad (E9)$$

$$SF_{COS}'(f)=[K\cdot B\cdot T\cdot\cos(\Theta)]\cdot\sin c(fT)+[(K\cdot B\cdot T\cdot\cos(\Theta))/2]\cdot(\sin c[(f-2f_o)T]+\sin c[(f+2f_o)T])-[(K\cdot B\cdot T\cdot\sin(\Theta))/2]\cdot(e^{-j\pi/2}\cdot\sin c[(f-2f_o)T]+e^{j\pi/2}\cdot\sin c[(f+2f_o)T]) \quad (E10)$$

FIG. 21 illustrates $SF_{SIN}'(f)$ according to the frequency f and FIG. 22 illustrates $SF_{COS}'(f)$ according to the frequency f.

In a third step of the demodulation process, the intermediate in phase demodulated signal $SF_{SIN}'$ and the intermediate in phase quadrature demodulated signal $SF_{COS}'$ are filtered by the respective low-pass filters 351, 352, which deliver at the output respectively a first in phase demodulated signal $SF_{SIN}$ and a first in phase quadrature demodulated signal $SF_{COS}$.

Each low-pass filter 351, 352 is translated by a function $H_{LP}(f)$ with a cut-off frequency fc set here at 110 Hz.

In a non illustrated improvement, each low-pass filter 351, 352 is followed by a smooth low-pass filter which is translated by a function $H_{LPsmooth}(f)$ illustrated in FIG. 23, with cut-off frequencies at $fc1=2\ f_0$, $fc2=4\ f_0$, etc. Each smooth low-pass filter allows to carry out an average out of the last twenty sampling points from the previous low-pass filter $H_{LP}(f)$ to increase the rejection of the signals at the cut-off frequencies multiple of $2\ f_0$.

The first in phase demodulated signal $SF_{SIN}$ and the first in phase quadrature demodulated signal $SF_{COS}$ satisfy the following equation (E11) and (E12), in the frequential field:

$$SF_{SIN}(f)=SF_{SIN}'(f)\cdot H_{LP}(f)\cdot H_{LPsmooth}(f)=[K\cdot B\cdot T\cdot\sin(\Theta)]\cdot\sin c(fT) \quad (E11)$$

$$SF_{COS}(f)=SF_{COS}'(f)\cdot H_{LP}(f)\cdot H_{LPsmooth}(f)=[K\cdot B\cdot T\cdot\cos(\Theta)]\sin c(fT) \quad (E12)$$

FIGS. 24 and 25 respectively illustrate signals $SF_{SIN}(f)$ and $SF_{COS}(f)$ according to the frequency f.

In the temporal field, these equations (E11) and (E12) are translated by the following equations (E13) and (E14):

$$SF_{SIN}(t)=Ks(t)=K\cdot B\cdot rect_T(t)\cdot\sin(\Theta) \quad (E13)$$

$$SF_{COS}(t)=Kc(t)=K\cdot B\cdot rect_T(t)\cdot\cos(\Theta) \quad (E14)$$

In a fourth step of the demodulation process, the first in phase demodulated signal $SF_{SIN}$ and the first in phase quadrature demodulated signal $SF_{COS}$ are injected in the calculation means 353, in order to calculate the module of the first analog detection signal $SAD1(t)$, which corresponds to the module of signal $[(SF_{SIN}(t)+SF_{COS}(t))^2]^{1/2}$; these steps of the demodulation process allowing to extract the amplification signal z(t) without being affected by the unknown phase shift introduced by the system.

The calculated module, corresponding to the first fluorescence value VALF generated at the output of the main signal acquisition/processing module 31, satisfies the following equation (E15):

$$VALF=\text{Module}[SAD1(t)], \text{ namely}$$

$$VALF=[Kc(t)^2+Ks(t)^2]^{1/2}$$

$$VALF=[(K\cdot B\cdot rect_T(t)\cdot\cos(\Theta))^2[K\cdot B\cdot rect_T(t)\cdot\sin(\Theta)]^2]^{1/2}$$

$$VALF=[(K\cdot B\cdot rect_T(t))^2\cdot(\cos(\Theta)^2+\sin(\Theta)^2)]^{1/2}$$

$$VALF=K\cdot B\cdot rect_T(t)$$

And hence, considering that $rect_T(t)=1$ for $t<T$ $$VALF=K\cdot B \quad (E15)$$

The same equations are repeated for the reference beam FR, and thus for the calculation of the second analog detection signal SAD2, of the second digital reference signal SRN and at last the second so-called reference value VALR.

Fourth, a comparison means (not illustrated) arranged at the output of the first acquisition/processing module 32 and the second acquisition/processing module 33 performs the calculation of the value of the RFU based on the first fluorescence values $VALF_{j,i}$ and the second reference values $VALR_{j,i}$ delivered at the output of these modules 32, 33, for each sinusoidal iteration (j corresponding to the number of iterations and taking values 0, 1, 2, as, for a reminder, three iterations are used for measuring fluorescence) and for a concentration in 4-MU numbered i.

For an iteration j, with a concentration i, the prior value of RFU, named $rfu_{j,i}$, satisfies the following equation (E16):

$$rfu_{j,i}=(x_{j,i}+rfu_{Offset}) \quad (E16)$$

Where $x_{j,i}$ satisfies the following equations:
in normal coordinates:

$$x_{j,i}=\left(\frac{((VALF_{j,i}-offset_{AiR})\cdot K_{OPT}^{FLUO})}{(VALR_{j,i}\cdot A_{OPT}^{REF})}\cdot K_{STRIP}\cdot K_{STD}\right)$$

in extended coordinates:

$$x_{j,i}=\left(\frac{((VALF_{j,i}-offset_{EXR})\cdot K_{OPT}^{FLUO})}{(VALF_{j,i}\cdot A_{OPT}^{REF})}\cdot\frac{C_{opt}^{FLUO}}{C_{opt}^{REF}}\cdot K_{STRIP}\cdot K_{STD}\right)$$

with
i=number of the concentration in 4-MU
j=number of the iteration (0, 1, 2)
$K_{OPT}^{FLUO}$=adjustment coefficient for the fluorescence ray calculated during the prior calibration process
$C_{opt}^{FLUO}$=adjustment coefficient in extended coordinates for the fluorescence ray calculated during the prior calibration process
$A_{OPT}^{REF}$=adjustment coefficient for the reference beam calculated during the prior calibration process
$C_{opt}^{REF}$=adjustment coefficient in extended coordinates for the reference beam calculated during the prior calibration process $K_{STD}$=adjustment coefficient of internal reading calculated during the auto-calibration $K_{STRIP}$=adjustment coefficient of reference optical position calculated during the optical calibration process $VALF_{j,i}$=first fluorescence value for the iteration j, obtained for the concentration i $VALR_{j,i}$=second reference value for the iteration j, obtained for the concentration i $offset_{AIR}$=first mean fluorescence value obtained for a reading in the air $offset_{EXR}$=first mean fluorescence value in extended coordinates obtained for a reading in the air $rfu_{Offset}$=value of offset RFU Then, after having calculated the j values of $rfu_{j,i}$, a polynomial conversion is performed as explained above, with reference to FIG. 13, relating to the conversion factor $F_{CONV}$.

For an iteration j, with a concentration i, the value of RFU after applying the conversion factor $F_{CONV}$, named $rfu_{j,i}^{CONV}$, satisfies the following equation (E17):

$$rfu_{j,i}^{CONV}=(rfu_{j,i})^4 \cdot a+(rfu_{j,i})^3 \cdot b+(rfu_{j,i})^2 \cdot c+ (rfu_{j,i}) \cdot d+(rfu_{j,i})^2 \cdot e \quad (E17)$$

Where a, b, c, d and e are constants, with for example:
a=1,3240745951716500 E−13;
b=−3,7686707018928200 E−09;
c=7,3337036404781100 E−07;
d=1,0311832028790600 E+00;
e=9,4239190294182200 E−01;
and where:
for a value of $rfu_{j,i}^{CONV}$ calculated with (E17) and higher than a threshold Rmax, here equal to the value of 23433, $rfu_{j,i}^{CONV}$ is set at the threshold value Rmax; and for a value of $rfu_{j,i}^{CONV}$ calculated with (E17) and lower than the threshold Rmax, $rfu_{j,i}^{CONV}$ remains equal to this calculated value.

Finally, the value of the required final RFU $RFU_i^{FIN}$, for a concentration i, is calculated by performing the average of $rfu_{j,i}^{CONV}$ with j taking the values 0, 1 and 2 without possibly taking into consideration a value of $rfu_{j,i}^{CONV}$ too far from the average.

At the end, the final equation (E18) is obtained:

$$RFU_i^{FIN} = \frac{\left(\sum_j^2 rfu_{j,i}^{CONV}\right)}{2} \quad (E18)$$

Fifth, this value of the final RFU $RFU_i^{FIN}$ is transmitted to an operating system, such as an outer computer terminal or a computer system integrated within an automated in vitro diagnosis instrument, for evaluating, with additional calculations, the concentration in analytes.

The invention claimed is:

1. A system for the in vitro detection and/or quantification by fluorometry of at least one analyte in a sample of fluid, the system comprising:
a radiation source emitting a main beam in a given wavelength called emission wavelength;
an optical splitter arranged at the output of the radiation source for splitting the main beam into a first sample-energizing beam and a second reference beam;
a first photodetector designed for providing a first analog detection signal in response to detecting a fluorescence ray emitted by the sample, in a so-called fluorescence wavelength as a result of the excitation induced by the first energizing beam;
a second photodectector designed for providing at the output a second analog detection signal in response to a detection of the second reference beam;
a generator outputting a sinusoidal carrier signal at a predefined frequency called carrier frequency, and at least one digital demodulation signal at this same carrier frequency, wherein the sinusoidal carrier signal is in the form of a set of several periodic sinusoidal iterations at the carrier frequency, a time difference between two consecutive iterations being higher than a period of sinusoidal iterations, and wherein a first iteration of the sinusoidal carrier signal is used to check if the first analog detection signal is above a predefined minimum threshold;
a digital/analog converter connected to the generator for converting the sinusoidal carrier signal into an analog modulation signal at the carrier frequency, wherein if said first analog detection signal is below said minimum threshold, a return loop is provided for reducing said analog modulation signal;
an amplitude modulator connected to the digital/analog converter and to the radiation source to modulate in amplitude the main beam at the carrier frequency by applying the analog modulation signal on said radiation source;
an analog/digital converter connected to the photodetectors to convert the first analog detection signal into a first digital fluorescence signal and the second analog detection signal into a second digital reference signal;
digital processing means connected to the generator and to the analog/digital converter, designed, on the one hand to process the first digital fluorescence signal by demodulation at the carrier frequency in order to calculate a first so-called fluorescence value characteristic of the amplitude of the fluorescence ray and, on the other hand, process the second digital reference signal by demodulation at the carrier frequency in order to calculate a second so-called reference value characteristic of the amplitude of the reference beam; and
a means for comparing the first fluorescence value and the second reference value to calculate a final result for establishing the detection and/or quantification of the analyte.

2. The system according to claim 1, wherein the digital processing means comprise: a first demodulation means designed for demodulating the first digital fluorescence signal by multiplying it by at least one digital demodulation signal at the carrier frequency, in order to generate at least one first demodulated fluorescence signal; and a first calculation means designed to calculate, based on at least one first demodulated fluorescence signal, one first so-called fluorescence value characteristic of the amplitude of the fluorescence ray.

3. The system according to claim 2, wherein the first demodulation means comprises:
a first multiplier by a digital demodulation signal at the carrier frequency and in phase with the sinusoidal carrier signal, said first multiplier being possibly followed by a first low-pass filter at a cut-off frequency lower than the carrier frequency, in order to output a first so-called in phase demodulated fluorescence signal; and
a second multiplier by a digital demodulation signal at the carrier frequency and in phase quadrature with respect to the sinusoidal carrier signal, said second multiplier being possibly followed by a second low-pass filter at the same cut-off frequency, in order to output a first so-called phase quadrature demodulated fluorescence signal;

and wherein the first calculation means, at the output of said first and second multipliers, calculates the first fluorescence value corresponding to the module of the sum of the first in phase demodulated fluorescence signal and the first phase quadrature demodulated fluorescence signal.

4. The system according to claim 3, wherein the digital processing means comprise, at the input of the first and second multipliers:
a notch filter centered on the carrier frequency in order to filter the first digital fluorescence signal and output a first filtered intermediate signal; and
a subtracter performing the subtraction of the first digital fluorescence signal and the first filtered intermediate signal, in order to generate a first filtered fluorescence signal, this first filtered fluorescence signal being injected in said first and second multipliers of the first demodulation means.

5. The system according to claim 1, wherein the digital processing means comprise:
a second demodulation means designed to demodulate the second digital reference signal by multiplying it by at least one digital demodulation signal at the carrier frequency in order to generate at least one second demodulated reference signal; and
a second calculation means designed to calculate, based on at least one second demodulated reference signal, the second reference value.

6. The system according to claim 5 wherein the second demodulation means comprises:
a first multiplier by a digital demodulation signal at the carrier frequency and in phase with the sinusoidal carrier signal, said first multiplier being possibly followed by a first low-pass filter at a cutoff frequency lower than the carrier frequency, so as to output a second so-called in phase demodulated reference signal; and
a second multiplier by a digital demodulation signal at the carrier frequency and in phase quadrature with respect to the sinusoidal carrier signal, said second multiplier being possibly followed by a second low-pass filter at the same cutoff frequency so as to output a second so-called phase quadrature demodulated reference signal;

and wherein the second calculation means at the output of said first and second multipliers, calculates the second reference value corresponding to the module of the sum of the second in phase demodulated reference signal and the second in phase quadrature demodulated reference signal.

7. The system according to claim 6 wherein the digital processing means comprise, at the output of a second analog/digital converter and at the input of said first and second multipliers:
a notch filter centered on the carrier frequency so as to filter the second digital reference signal and output a second filtered intermediate signal; and
a subtracter performing the subtraction of the second digital reference signal and the second filtered intermediate signal so as to generate a second filtered reference signal, this second filtered reference signal ($SRN_0$) being injected in said first and second multipliers of the second demodulation means.

8. The system according to claim 1, further comprising, interposed between the radiation source and the optical splitter, an optical band-pass filter centered substantially on the emission wavelength.

9. The system according to claim 1, further comprising, interposed between the sample and the first photodetector, an optical band-pass filter centered substantially on the fluorescence wavelength.

10. The system according to claim 9, further comprising, interposed between the optical band-pass filter and the first photodetector, a waveguide achieved in the form of a guiding cone.

11. The system according to claim 1, further comprising, interposed between the optical splitter and the second photodetector, an optical low-pass filter which exhibits a low-wavelength cutoff substantially lower than the emission wavelength.

12. The system according to claim 11, further comprising, interposed between the optical low-pass filter and the second photodetector, a waveguide achieved in the form of a guiding cone.

* * * * *